(12) United States Patent
Morimoto et al.

(10) Patent No.: US 6,224,568 B1
(45) Date of Patent: May 1, 2001

(54) DUAL-CHAMBER TYPE INJECTOR AND CONNECTOR USED THEREFOR

(75) Inventors: Shuji Morimoto; Kazuhiro Okochi, both of Suita; Kotaro Wakamatsu, Takarazuka; Nobuyoshi Tanaka, Hirakata, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/083,201

(22) Filed: May 22, 1998

(30) Foreign Application Priority Data

Jun. 3, 1997 (JP) .................................................. 9-144849
Feb. 20, 1998 (JP) ................................................ 10-038221

(51) Int. Cl.$^7$ ................................................. A61M 37/00
(52) U.S. Cl. ............................................ 604/89; 604/905
(58) Field of Search ........................... 604/82–84, 86–92, 604/905

(56) References Cited

U.S. PATENT DOCUMENTS

| | | | |
|---|---|---|---|
| 4,048,999 | 9/1977 | Köbel | 128/272.1 |
| 4,493,348 | * 1/1985 | Lemmons | 141/1 |
| 4,568,346 | 2/1986 | van Dijk . | |
| 5,330,426 | * 7/1994 | Kriessel et al. | 604/89 |
| 5,425,465 | * 6/1995 | Healy | 215/355 |
| 5,429,256 | 7/1995 | Kestenbaum | 215/247 |
| 5,472,022 | * 12/1995 | Michel et al. | 141/1 |
| 5,566,729 | 10/1996 | Grabenkort et al. | 141/25 |
| 5,569,209 | 10/1996 | Roitman | 604/190 |

FOREIGN PATENT DOCUMENTS

| | | |
|---|---|---|
| 0 324 257 | 7/1989 | (EP) . |
| 2315149 | 1/1977 | (FR) . |
| 1419061 | 12/1975 | (GB) . |

* cited by examiner

Primary Examiner—John D. Yasko
(74) Attorney, Agent, or Firm—Wenderoth, Lind & Ponack, L.L.P.

(57) ABSTRACT

A needle connecting portion of a syringe which includes a drug accommodating chamber accommodating a first component is arranged opposite to a takeout port of a hermetically closed container which includes a container chamber accommodating a second component. The syringe is connected to the container through a connector so as to be movable in mutual proximity and adapted to be separable from the connector. There is provided a communication passage capable of communicating the drug accommodating chamber with the container chamber. The communication passage is cut off by a closure member arranged between both of the chambers. The syringe and the container chamber are moved in proximity to each other, thereby displacing the closure member so as to open the communication passage. An injector of the present invention is compact in shape but can surely retain sterility while being stored and surely mix both of the components accommodated therein through a simple operation just before administration. Further, it can prevent the sharpness of an injection needle from being damaged at the time of a mixing operation and easily remove a syringe after the mixing operation.

6 Claims, 28 Drawing Sheets

F I G. 3
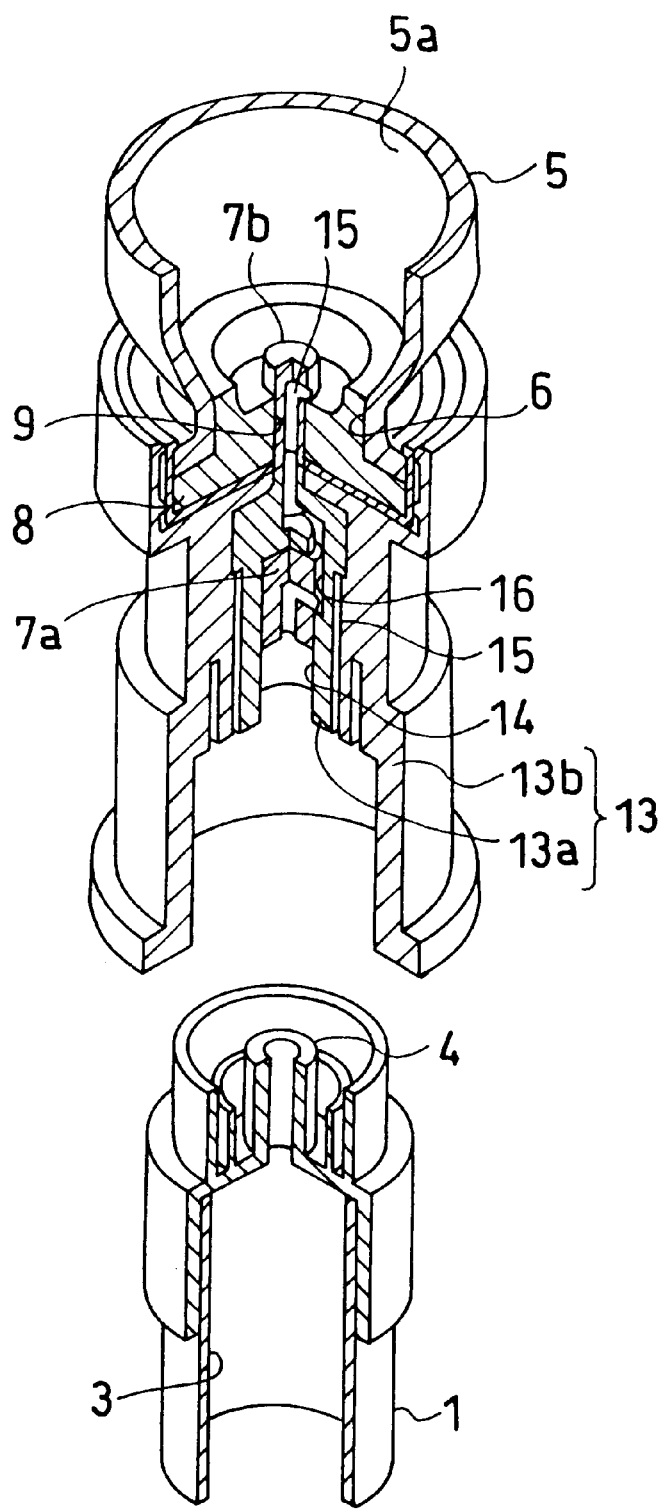

F I G. 17
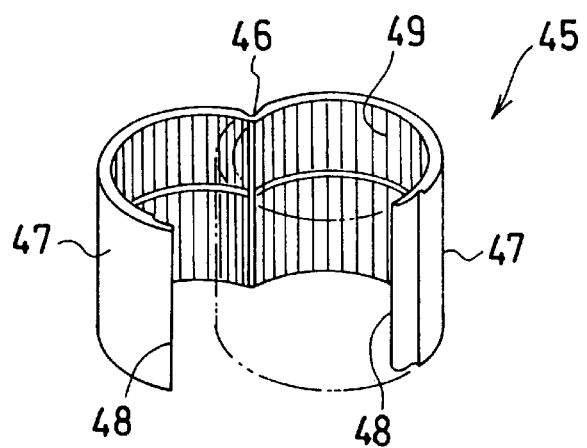
F I G. 18
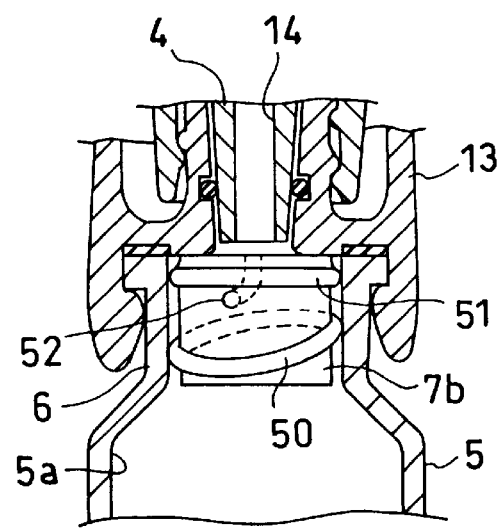

F I G. 2 4
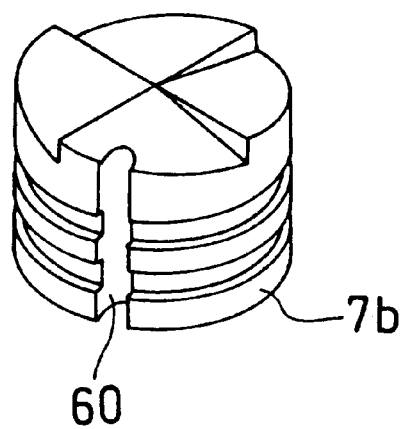

F I G. 2 6
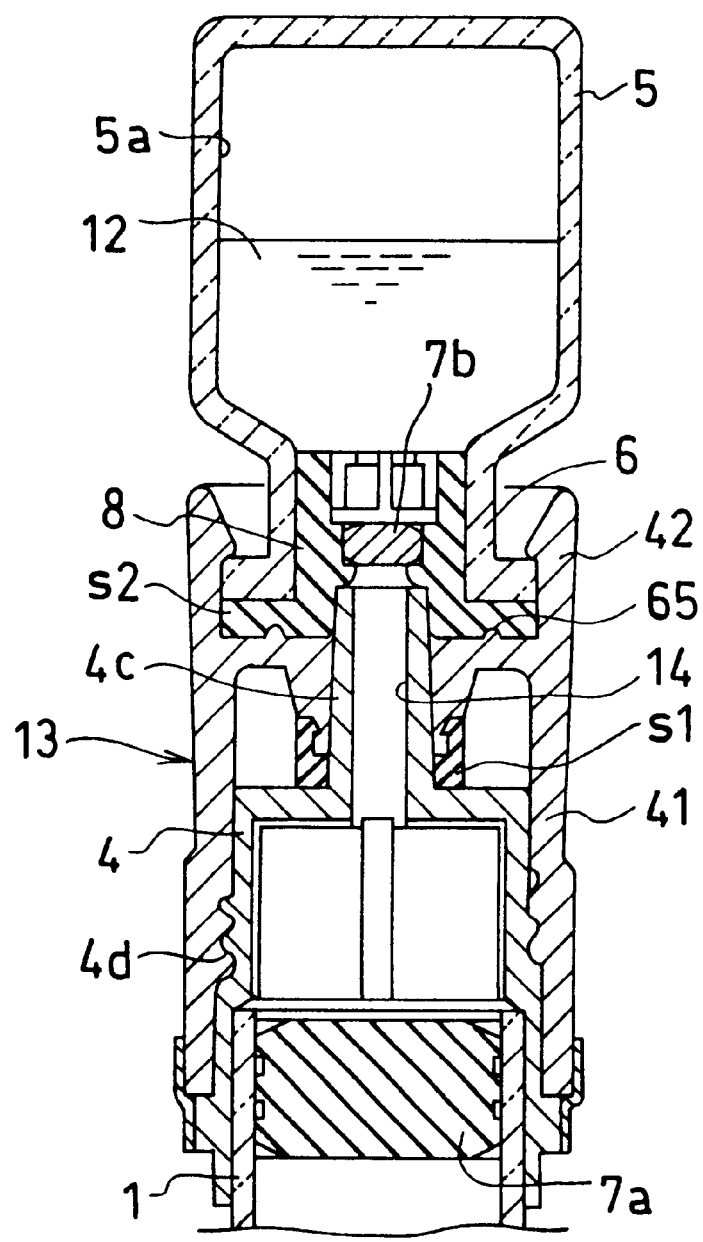

DUAL-CHAMBER TYPE INJECTOR AND CONNECTOR USED THEREFOR

BACKGROUND OF THE INVENTION

1. Field of the Invention

The present invention relates to a dual-chamber type injector accommodating two components, an injection drug and its dissolving liquid, within, respectively, a syringe and a hermetically closed container such as a vial or the like separately from each other and to a connector used for this dual-chamber type injector. More specifically, it is directed to an injector and a connector used therefor, the injector being compact in shape but able to assuredly retain sterility while being stored and to mix both of the accommodated components surely through a simple operation just before administration. Further, the injector is unlikely to damage the sharpness of an injection needle during a mixing operation and is capable of removing the syringe simply after the mixing operation.

2. Description of the Prior Art

Some of the drugs to be administered by injection change in quality over time if dissolved in a dissolving liquid or the like. Therefore, generally a powder injection drug is stored in a dry state and mixed with and dissolved in a dissolving liquid just before administering it.

Ordinarily, the powder injection drug and its dissolving liquid are hermetically packed, for example, in, respectively, a vial and an ampul separately from each other. When they are used for administration, first an injector sucks the dissolving liquid within the ampul and pours it into the vial to dissolve the powder injection drug therein, and then sucks the dissolved drug again. However, these mixing and dissolving operations are troublesome. Besides, an injection needle pierces a vial's closure member in contact with the air, so that it is not easy to keep the injection needle and the mixed injection drug sterile.

In order to solve the above problems, there exists, for example, an injector previously proposed and disclosed in Japanese Patent Public Disclosure No. 5-31189 by the present Applicant as a dual-chamber type injector which incorporates two components and a syringe integrally thereinto so as to facilitate the mixing operation in a sterile state.

The above-mentioned conventional dual-chamber type injector, for example, as shown in FIG. 32, has a syringe 83 accommodating a first powder component 81 slidably inserted from an opening 87 provided at a rear end of an external cylinder 86 and hermetically seals a drug accommodating chamber 85 within the syringe 83 by embedding a front end of an injection needle 84 in a sealing member 88 provided at a front end of the external cylinder 86. The external cylinder 86 supports a hermetically closed container 89 which includes a container chamber 96 accommodating a second liquid component 82. A closure member 91 attached to a takeout port 90 of the container 89 is intimately contacted with the sealing member 88 and a cover 92 is attached to the opening 87 at the rear end of the external cylinder 86 so as to airtightly cover the syringe 83.

The cover 92 has a flange portion 93 formed with an annular easily-broken portion 94.

With the foregoing dual-chamber type injector 80, when an external force is applied to a rear end of the cover 92, for example, by pushing the external cylinder 86 onto a desk from above, the easily broken portion 94 breaks. If it is further pushed, a piston 95 is pressed to increase the inner pressure of the drug accommodating chamber 85 and at the same time relatively move the syringe 83 while sliding it toward the container 89. Then the front end of the injection needle 84 enters the container chamber 96 by piercing the sealing member 88 and the closure member 9 1, thereby allowing gas to flow from the drug accommodating chamber 85 into the container chamber 96 to result in increasing the pressure within the container chamber 96.

Next, if the foregoing pushing force is cancelled, the increased pressure within the container chamber 96 retracts the piston 95 and causes the second liquid component 82 to flow into the drug accommodating chamber 85 through the injection needle 84. The first powder component 81 is mixed with and dissolved in this flowed-in second component 82.

Subsequently, excessive gas flowed into the syringe 83 is discharged by operating the piston 95 and then the syringe 83 is extracted from the external cylinder 86 to be used for drug administration.

3. Problems Presented by the Prior Art

The conventional dual-chamber type injector has the following problems:

(1) Since the hermetically closed container is arranged ahead of the injection needle attached to the front end of the syringe through the sealing member, the injector becomes large in its entire length and is therefore bulky when stored.

(2) A metal injection needle is fixed to the front end of the syringe; it is not easy to dispose of the metal injection needle separately from the other non-metallic portions after the injector is used.

(3) The drug accommodating chamber is communicated with the container chamber through a slot within the injection needle. Accordingly, the drug or the like does not readily move and therefore requires much time for movement. In addition, the powder drug clogs the slot to interrupt the communication between the drug accommodating chamber and the container chamber, causing a fear of failure to assuredly mix both components.

(4) When mixing both the components, the injection needle has to pierce through the sealing member and the closure member. This is likely to produce rubber dust or the like when piercing and to decrease the sharpness of the injection needle. Accordingly, the injection needle cannot easily pierce the skin of a patient and additionally may give great pain to the patient.

(5) When the syringe is dismantled from the connector after the mixing operation, it is necessary to straightly extract the injection needle from the sealing member or the closure member so as not to apply an excessive external force to the injection needle, and therefore a careful operation is needed.

SUMMARY OF THE INVENTION

The present invention has a technical object of solving the foregoing problems and providing a dual-chamber type injector and a connector used therefor. The dual-chamber type injector is compact in shape but can assuredly retain its sterility while being stored and mix both of accommodated components surely through a simple operation just before administration. Further, the injector is unlikely to damage the sharpness of an injection needle when conducting the mixing operation and has a syringe to be easily removed after the mixing operation.

In order to solve the foregoing problems, the present invention has constructed a dual-chamber type injector and a connector used therefor as follows.

A first invention relates to a dual-chamber type injector comprising a syringe 1 including a drug accommodating chamber 3 which accommodates a first component 11 and having a needle connecting portion 4 with an injection needle 10 not yet attached thereto. The needle connecting portion 4 is arranged opposite to a takeout port 6 of a hermetically closed container 5 including a container chamber 5a which accommodates a second component 12. The syringe 1 is connected and fixed to the container 5 through a connector 13 so as to be movable in proximity mutually. At least the syringe 1 is adapted to be separable from the connector 13, there being provided a communication passage 14 capable of communicating the drug accommodating chamber 3 with the container chamber 5a. The communication passage 14 is cut off by a closure member 7a, 7b arranged between both of the chambers 3 and 5a. The syringe 1 and the container 5 can be moved in proximity to each other, thereby displacing at least part of the closure member 7, 7a, 7b so as to be able to open the communication passage 14.

According to the first invention, the closure member cuts off the communication passage provided between the drug accommodating chamber and the container chamber so that the first component and the second component are hermetically accommodated separately from each other in the drug accommodating chamber and the container chamber, respectively.

When the syringe and the container chamber are moved in proximity to each other just before administration, the closure member is displaced to open the communication passage to thereby communicate the drug accommodating chamber with the container chamber through this communication passage, with the result of moving the liquid component accommodated in one chamber to the other chamber and mixing both components with each other.

At this time the injection needle is not attached to the needle connecting portion of the syringe so that the communication passage can be wide over its entire length to result in smoothly moving the liquid component into the other chamber.

After the mixed and dissolved components have been accommodated in the drug accommodating chamber, the syringe is separated from the connector and the injection needle is attached to the needle connecting portion. Subsequently, excessive gas that flowed into the syringe is expelled to complete the preparations for drug administration.

A second invention comprises supporting a piercing member 30 with the takeout port 6 opposite to the closure member 7a, 7b and forming an engaging portion 31 on a periphery of a leading end side of the piercing member 30. The closure member 7a, 7b is moved to make the piercing member 30 pierce it so as to be able to open the communication passage 14 and engage with an engaging portion 31.

According to the second invention, the piercing member pierces the closure member to form a communication hole of a desired size therein to thereby open the communication passage. The syringe is separated from the connector after the mixing operation. In a case where the closure member pierced by the piercing member remains in the container chamber, the injection needle is attached to the needle connecting portion with the closure member remaining therein. However, in a case where the closure member is left in the syringe, the injection needle is attached to the needle connecting portion after the closure member has been removed. The other operations and motions are the same as those of the first invention.

In a case where an engaging portion is provided on a periphery of a leading end side of the piercing member, at the time of the communicating operation the closure member is engaged with the piercing member through the engaging portion and the piercing member is supported by the takeout port of the container chamber. As a result, when separating the syringe from the connector, the closure member is assuredly removed from the syringe to remain in the container chamber. Therefore, after having separated the syringe from the connector, the injection needle can be attached to the needle connecting portion without removing the closure member, and accordingly this case is more preferable.

A third invention relates to a dual-chamber type injector comprising a syringe 1 including a drug accommodating chamber 3 which accommodates a first component 11 and having a needle connecting portion 4 with an injection needle 10 not yet attached thereto. The needle connecting portion 4 is arranged opposite to a takeout port 6 of a hermetically closed container 5 including a container chamber 5a which accommodates a second component 12. The syringe 1 is connected and fixed to the container 5 through a connector 13, at least the syringe 1 being adapted to be separable from the connector 13. There is provided a communication passage 14 capable of communicating the drug accommodating chamber 3 with the container chamber 5a. The communication passage 14 is cut off by a closure member 7a, 7b arranged between both of the chambers 3 and 5a. A piston disposed within the syringe 1 to be pushed to increase the inner pressure of the syringe 1 to displace at least part of the closure member 7a, 7b toward the container 5 so as to be able to open the communication passage 14.

A fourth invention relates to a connector used with the third invention, and comprises a cylindrical body 40 having a syringe fixing portion 41 formed at one end. The needle connecting portion 4 of the syringe 1 is fixed to the syringe fixing portion 41 so as to be separable therefrom. The cylindrical body 40 has a container fixing portion 42 formed at its other end. The takeout port 6 of the hermetically closed container 5 is fixed to the container fixing portion 42 opposite to an opening 4b at a front end of the needle connecting portion 4. Sealing members s1, s2, s3 are arranged between the cylindrical body 40 and the needle connecting portion 4 as well as between the cylindrical body 40 and the container 5 to airtightly shield a space between the needle connecting portion 4 and the takeout port 6 from an external space. The pressure of a fluid flowing out of the front end of the needle connecting portion 4 with the inner pressure of the syringe 1 increased displaces at least part of a closure member 7b, hermetically sealing the takeout port 6 into the container 5 so as to be able to communicate the container chamber 5a within the container 5 with the drug accommodating chamber 3 within the syringe 1.

A fifth invention relates to a connector used for the third invention as well as for the fourth invention, and comprises a cylindrical body 40 has a syringe fixing portion 41 formed at its one end, the needle connecting portion 4 of the syringe 1 being fixed to the syringe fixing portion 41 separably therefrom. The cylindrical body 40 has a container fixing portion 42 formed at its other end, the takeout port 6 of the hermetically closed container 5 being fixed to the container fixing portion 42 opposite to an opening 4b at a front end of the needle connecting portion 4. A sealing member s4 is arranged between the needle connecting portion 4 and the container 5 to airtightly shield a space between the needle connecting portion 4 and the takeout port 6 from an external space. The pressure of a fluid flowing out of the front end of the needle connecting portion 4, with the inner pressure of the syringe 1 increased, displaces at least part of a closure member 7b hermetically sealing the takeout port 6 into the container 5 so as to be able to communicate the container chamber 5a within the container 5 with the drug accommodating chamber 3 within the syringe 1.

In the third, fourth and fifth inventions, the syringe is surely connected and fixed to the hermetically closed container through the connector, and the sealing member or members airtightly close the space between the needle connecting portion and the takeout port while the injector is being stored.

Just before administration, the piston within the syringe is pressed to increase the inner pressure of the syringe with the result of the fluid flowing out of the front end of the needle connecting portion. The pressure of the flowing fluid displaces the closure member hermetically sealing the takeout port into the container chamber to thereby open the communication passage. The other operations and motions are the same as those of the first invention.

Advantageously, the sealing member airtightly shields a wide area of the needle connecting portion from the external space to retain sterility. On the other hand, after having performed the communication, the sealing member is preferably arranged at a portion near to an opening at a front end of a nozzle portion of the needle connecting portion so that the liquid might not splash or leak out of the nozzle portion when it passes through the communication passage.

An airtight sealing member may be arranged at least outwardly of an injection needle fixing threaded portion of the needle connecting portion and at the same time the communication passage may be liquid-tightly shielded from the external space at a portion near to the front opening of the nozzle portion. This arrangement can keep a wide area of the needle connecting portion sterile and prevent the liquid from splashing or leaking out of the nozzle portion.

As for the first and second components mentioned in the present invention, it is sufficient if at least either of them is liquid, and both may be liquid. In the case where only one of them is liquid, preferably the other has a formulation that is able to easily dissolve, such as powder, a solid agent obtained by freeze drying or the like.

The following concrete examples can be listed as an injection drug comprising both of the above components and able to be administered by the dual-chamber type injector of the present invention, namely a bioactive substance:

bioactive peptide; anti-tumor agent; antibiotic; antipyretic agent; analgestic agent; anti-inflammatory agent; antitussive and expectorant agent; sedative; muscle relaxant; anti-epilepsy agent; anti-ulcer agent; antidepression agent; anti-allergic agent; cardiac, arrhythmia therapeutic agent; vasodilator; antihypertensive and diuretic agent; diabetes therapeutic agent; anti-lipemia agent; anti-blood clotting agent; hemostatic; anti-tuberculosis agent; hormone agent; antinarcotic; bone resorption inhibitor; osteogenesis promoter; and blood-vessel-growth inhibitor.

Needless to say, it is not limited to these.

Further, the following are examples of the bioactive peptide:

luteinizing hormone releasing hormone (LH-RH) and its analogues; LH-RH agonist or LH-RH antagonist; insulin; erythropoietin; somatostatin; somatostatin derivatives; growth hormone; human growth hormone; prolactin; adrenocorticotropic hormone (ACTH); ACTH derivatives (such as ebiratide), melanocyte stimulating hormone (MSH); and thyroid hormone releasing hormone [expressed in a structural formula of(Pyr)Glu-His-Pro-NH$_2$ and sometimes abbreviated as 'TRH'], its salts and derivatives.

Moreover, examples of the osteogenesis promoter are as follows:

(2R,4S)-(—)-N-[4-(diethoxyphosphorylmethyl)phenyl]-1,2,4,5-tetrahydro-4-methyl-7,8-methylenedioxy-5-oxo-3-benzothiepine-2-carboxamide, its salts and derivatives.

Each of the above-mentioned bioactive substances may be used as it is or as a pharmacologically acceptable salt. For example, in the case of a bioactive substance having a basic group such as an amino group, its salt with an inorganic acid (e.g., hydrochloric acid, sulfuric acid, nitric acid or the like) or an organic acid (e.g., carbonic acid, succinic acid or the like) is used. Further, in the case of a bioactive substance having an acid group such as carboxyl group, its salt with an inorganic base (e.g., natrium, potassium or the like alkaline metals) or an organic base (e.g., triethylamine or the like organic amines, arginine or the like basic amino acids) is used.

However, the bioactive substances to be used for the dual-chamber type injector according to the present invention are preferably bioactive peptides and more preferably the LH-RH or its analogues. Leuprorelin or leuprorelin acetate is particularly preferable.

The closure member of the present invention is satisfactory if at least its part is adapted to be able to open the communication passage when displaced. Generally, a rubber closure is used but it may be a sealing member in the shape of a film. Further, the closure member may be formed from a single closure member but may be composed of a first closure member hermetically sealing the drug accommodating chamber and a second closure member hermetically sealing the container chamber. In the latter case, each chamber can be hermetically sealed easily and independently. Besides, since the respective chambers are completely separated from each other by different closure members, even if the liquid component is sterilized with heated vapour, the moisture adsorbed to the closure member hermetically sealing this liquid component is unlikely to exert a bad influence on the other component such as powder.

In the fourth or the fifth invention, it suffices if the needle connecting portion is separably fixed to the syringe fixing portion. Therefore, this fixing construction is not limited to a particular one. For example, the syringe fixing portion is provided with a threaded portion into which the needle connecting portion may be screwed. Alternatively, the syringe fixing portion and the needle connecting portion are provided with a first engaging portion and a second engaging portion, respectively. And the needle connecting portion may be fixed to the syringe fixing portion by engaging the first engaging portion with the second engaging portion.

Preferably, the syringe fixing portion is fixed to the needle connecting portion so as not to move the cylindrical body and the needle connecting portion relative to each other, for example by winding an adhesive tape over the connector and the syringe or attaching an annular engaging member able to prevent relative rotation, in order that the sealing member or members can have a shield from the external space surely while they are being stored or the like.

The sealing members employed in the fourth or the fifth invention are satisfactory if they can hermetically seal the spaces between the cylindrical body and the needle connecting portion or the hermetically closed container. Each of them may be an annular rubber packing or constructed from an elastic structure formed by applying, to at least one of the cylindrical body, the needle connecting portion and the hermetically closed container, a lining agent such as a copolymer of vinyl chloride and vinyl acetate, and gelatinizing it.

Moreover, in the event that only part of the closure member attached to the takeout port of the hermetically closed container is adapted so as to be movable into the container chamber, the remaining unmovable portion may be made to serve as the aforesaid sealing member.

It is possible to use a separately prepared common injection needle as the injection needle to be attached to the front end of the syringe. Alternatively, an exclusive injection needle may be integrally packed into the dual-chamber type injector by putting it along the injector or accommodating it within the piston rod.

Since the present invention is constructed as mentioned above, it produces the following effects.

(A) A container chamber is arranged opposite to a syringe having a needle connecting portion with no injection needle attached thereto and no injection needle is positioned therebetween. Therefore, the injector can be reduced in length by the amount corresponding to a length of an injection needle to be attached while being stored, and therefore the storage space can be made compact.

Particularly, the third and fourth inventions merely fix the syringe and a hermetically closed container to a connector without constructing them so as to be slidable relative to the connector. Accordingly, it is possible to downsize the connector and make the storage space more compact.

(B) It is possible to reliably hermetically accommodate respective components separately from each other while storing them and therefore surely retain sterility.

Particularly, the third and fourth inventions, as well as the fifth invention, need not make the syringe and the hermetically closed container slidable relative to the connector. Consequently, it is possible to more surely retain sterility between the needle connecting portion and a takeout port with a simple construction in which sealing members are arranged between a cylindrical body and the needle connecting portion and the hermetically closed container or between the needle connecting portion and the hermetically closed container.

(C) Particularly, the fourth invention makes it sufficient to only arrange sealing members between the needle connecting portion and the hermetically closed container. With such a simple construction, sterility between the needle connecting portion and the takeout port can be reliably retained.

(D) Just before administration, a closure member is displaced to open a communication passage by moving the syringe and the container chamber in proximity to each other according to the first or the second invention or pushing the piston according to the third invention. Either case can mutually mix and dissolve both of the components through a simple operation.

Each of the above inventions attaches no injection needle to a portion between the syringe and the container chamber and therefore can make the communication passage wide over its entire length. As a result, even if a component such as a powder drug invades the communication passage, clogging is unlikely to occur and a liquid component can smoothly move at the time of mixing. This invites the possibility of surely mixing both components.

(E) Since the present invention does not use any injection needle when conducting the mixing operation, unlike the prior art which pierces the closure member or the like with an injection needle on effecting the mixing operation, there is no likelihood that rubber dust or the like is produced and the sharpness of the injection needle is not damaged.

(F) The syringe is adapted to be separable from the connector, and in addition no injection needle is attached to the needle connecting portion. Accordingly, the syringe can be easily removed from the connector or the hermetically closed container just by cancelling the above fixing connection.

(G) Being constructed so as to have an injection needle attached to a front end of the syringe when administering, the present invention can easily separate the injection needle from the syringe after it has been used, and therefore can readily discriminate the metal injection needle from non-metallic portions for disposal, unlike the above-mentioned conventional technique.

BRIEF DESCRIPTION OF THE DRAWINGS

FIG. 3 is a partly broken perspective view showing the neighborhood of a connector of the first embodiment with the syringe removed therefrom after the mixing operation;

FIG. 17 is a perspective view of an annular engaging member;

FIG. 18 illustrates a first modification of the sixth embodiment and is an enlarged sectional view showing the neighborhood of a takeout port;

FIG. 24 is an enlarged perspective view showing a modification of a second closure member of the eighth embodiment;

FIG. 26 illustrates a dual-chamber type injector of a tenth embodiment corresponding to the third and fourth inventions and is a vertical sectional view showing the neighborhood of a connector;

DETAILED DESCRIPTION OF THE PREFERRED EMBODIMENTS

Hereafter, embodiments of the present invention will be explained with reference to the drawings.

(First Embodiment)

Figure 1:
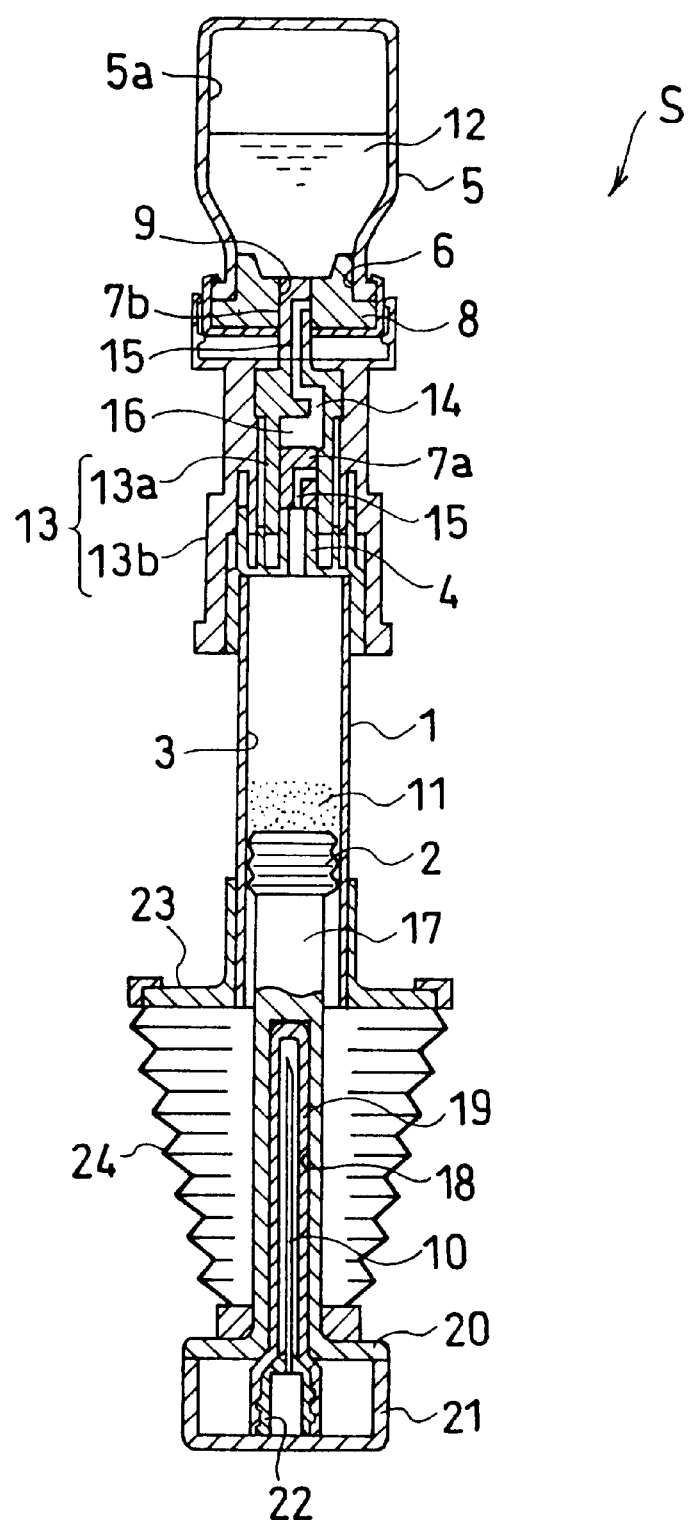
FIG. 1 illustrates a dual-chamber type injector of a first embodiment corresponding to a first invention and is a sectional view of the injector while being stored.
Figure 2:
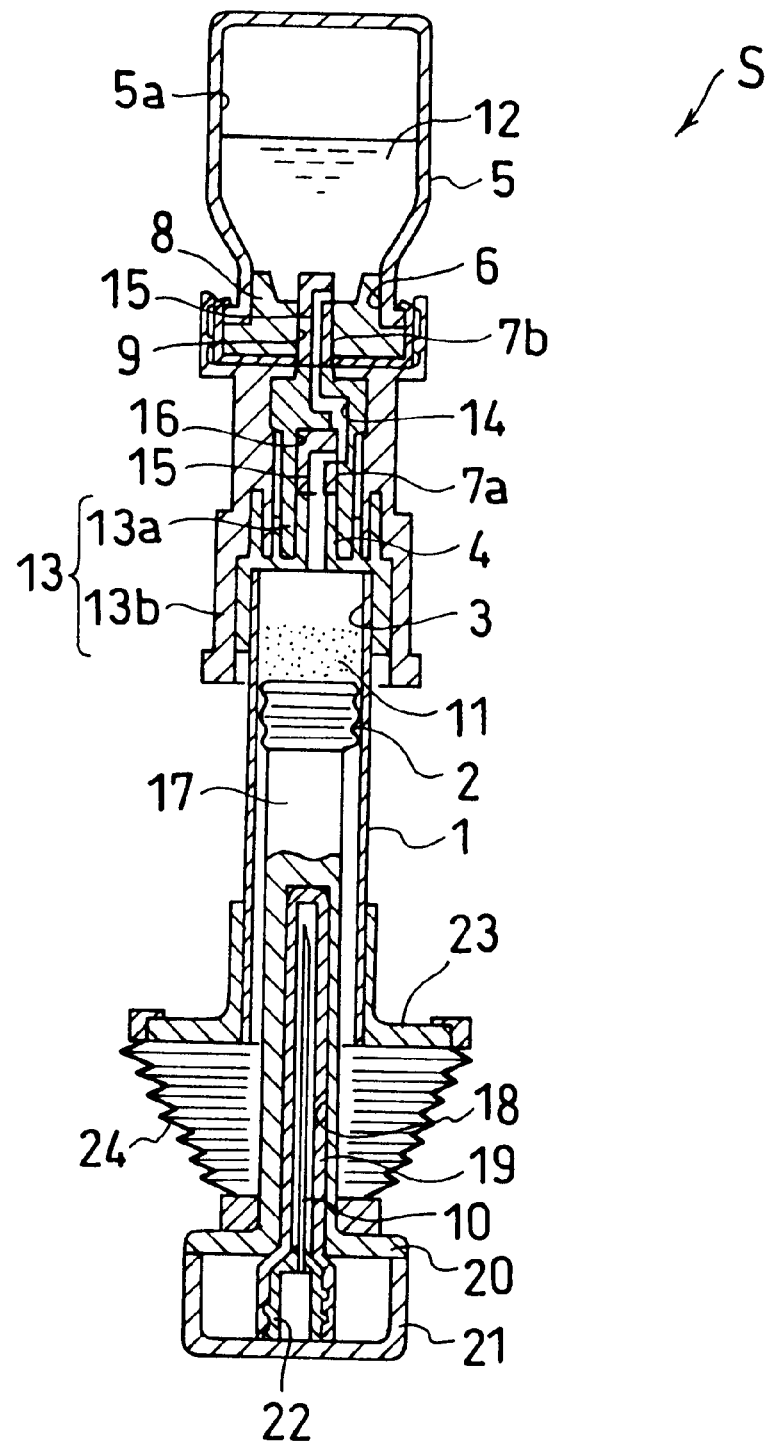
FIG. 2 is a sectional view showing the injector of the first embodiment during the process of a mixing operation.

FIGS. 1 to 3 show a dual-chamber type injector of a first embodiment corresponding to a first invention. FIG. 1 is a sectional view of the injector while being stored. FIG. 2 is a sectional view of the injector during the process of a mixing operation. FIG. 3 is a partly broken perspective view showing the neighborhood of a connector with a syringe removed therefrom after the mixing operation.

As shown in FIG. 1, a dual-chamber type injector (S) comprises a syringe 1 having a rear end into which a piston 2 is internally fitted and including a drug accommodating chamber 3. The drug accommodating chamber 3 accommodates a powder drug 11 of a first component.

No injection needle is attached to a needle connecting portion 4 at a front end of the syringe 1 but a connector 13 is separately attached at its one end side to the syringe 1. On the other hand, a takeout port 6 of a hermetically closed container 5 such as a vial or the like is attached to the other end side of the connector 13 opposite to the needle connecting portion 4. The container 5 and the syringe 1 are arranged so as to be movable in proximity to each other. The container 5 includes a container chamber 5a which accommodates a dissolving liquid 12 of a second component.

Provided in the connector 13 between the drug accommodating chamber 3 and the container chamber 5a is a communication passage 14 capable of communicating both chambers (3, 5a) with each other. Closure members 7a and 7b arranged between both chambers 3 and 5a cut off the communication passage 14.

More specifically, a first closure member 7a is slidably arranged on a syringe side of the communication passage 14 and hermetically seals an opening at a front end of the needle connecting portion 4. Formed in the first closure member 7a is a communication hole 15, which is adjusted to open when the first closure member 7a is pushed into the communication passage 14 to reach an intermediate chamber 16.

In the first embodiment, the connector 13 is composed of an inner cylindrical portion 13 a and an outer cylindrical portion 13b. The needle connecting portion 4 of the syringe 1 and the hermetically closed container 5 are attached to the opposite ends of the outer cylindrical portion 13b. The communication passage 14 is formed in the inner cylindrical portion 13a. However, needless to say, the connector of the present invention may comprise these portions formed into an integral structure.

The takeout port 6 of the container 5 is hermetically sealed by a sealing closure 8. Formed in the sealing closure 8 at the mid portion thereof is a through hole 9, into which a second closure member 7b is slidably fitted. The second closure member 7b projects from an outer surface of the sealing closure 8 to intimately contact with the connector 13. The second closure member 7b is adapted to be relatively displaced into the container chamber 5a by moving the container 5 toward the connector 13. This second closure member 7b is also provided with the same communication hole 15 as that of the first closure member 7a. This communication hole 15 has one end opened toward the communication passage 14 and the other end adjusted to open within the container chamber 5a by the movement of the second closure member 7b into the container chamber 5a.

An injection needle 10 of the dual-chamber type injector (S) is not attached to the needle connecting portion 4 at the front end of the syringe 1 as mentioned above, but is inserted into an accommodating portion 18 formed within a piston rod 17 while being covered with a protector 19. Fixed to a pushing portion 20 of the piston rod 17 is a protecting case 21 which hermetically encloses a hub 22 of the injection needle 10 so as to protect it.

Additionally, attached between the pushing portion 20 and a finger grip 23 disposed at a rear end of the syringe 1 is an extendable accordion cover 24, which keeps an outer surface of the piston rod 17 and an inner surface of the syringe 1 sterile.

The first embodiment accommodates, within the piston rod 17, the injection needle 10 covered with the protector 19. However, this injection needle 10 may be replaced with a separately packed common injection needle.

The extendable cover is also applicable to such a case where the injection needle is attached to the front end of the syringe as in the above-mentioned prior art. Thus it is possible to keep the outer surface of the piston rod and the inner surface of the syringe sterile with the result of being able to prevent a danger such as in-hospital infection before it occurs. However, even in the present invention, should there be no likelihood of polluting the inner surface of the syringe and so on, like a case where the injector is packed to be sterile in its entirety and used immediately after being opened, the extendable cover may be omitted.

Next, explanation is made as to the operation for mixing the powder drug 11 with the dissolving liquid 12 and dissolving it therein with the dual-chamber type injector (S).

First, the injector (S) is arranged so that the protecting case 21 fixed to the rear end of the piston rod 17 is directed downward and the hermetically closed container 5 is oriented upward. Then the protecting case 21 is pressed against, for example, an upper surface of a desk and the container 5 is pushed downward while being held.

Consequently, the piston 2 ascends within the syringe 1 to increase the inner pressure of the syringe 1 and at the same time the syringe 1 and the container 5 are moved in proximity to each other. The first closure member 7a is pushed by the needle connecting portion 4 to ascend through the communication passage 14 until it reaches the intermediate chamber 16 and the second closure member 7b is pushed back by the connector 13 to ascend through the hole 9. Then the injector (S) reaches a state as shown in FIG. 2.

As a result, the communication passage 14 is opened to communicate the drug accommodating chamber 3 with the container chamber 5a, thereby allowing compressed gas within the syringe 1 to flow into the container chamber 5a through the communication passage 14 to result in increasing the inner pressure of the container chamber 5a as well.

Then if the pushing force is cancelled, the piston 2 is pushed back to decrease the inner pressure of the syringe 1 to result in pushing out the dissolving liquid 12 by the increased inner pressure of the container chamber 5a. The thus pushed out dissolving liquid 12 flows into the drug accommodating chamber 3 within the syringe 1 through the communication passage 14 to be mixed with the powder drug 11 and dissolves it. Should a first pushing operation be unable to move the whole amount of the dissolving liquid 12 into the drug accommodating chamber 3, repetition of the above pushing and cancelling operations can fulfill that purpose.

When the above operation has moved the whole amount of the dissolving liquid 12 into the drug accommodating chamber 3 to make it mix with and dissolve the powder drug 11 homogeneously, after having expelled excessive gas flowed into the syringe 1 by operating the piston rod 17, the syringe 1 is pulled backward to be separated from the connector 13 as shown in FIG. 3. At this time, since the first closure member 7a is left in the connector 13, the front end of the needle connecting portion 4 is exposed and therefore the injection needle 10 taken out of the piston rod 17 with the protector 19 can be attached to this needle connecting portion 4 as it is.

Figure 4:
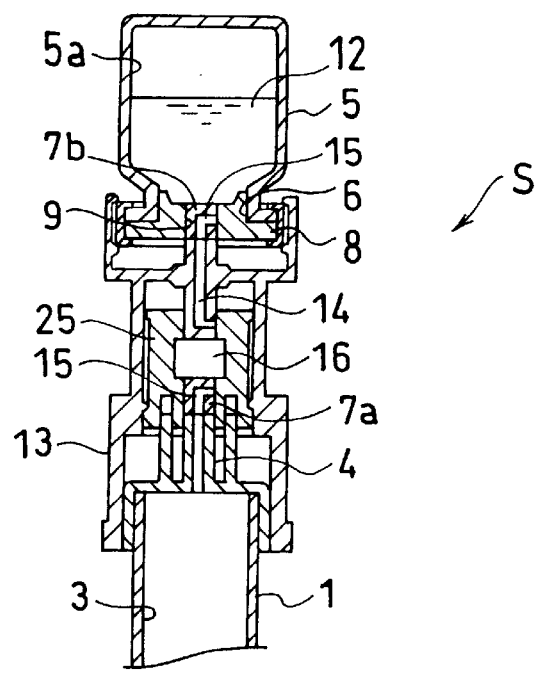
FIG. 4 illustrates a modification of the first embodiment and is a sectional view showing principal parts of a dual-chamber type injector while being stored.
Figure 5:
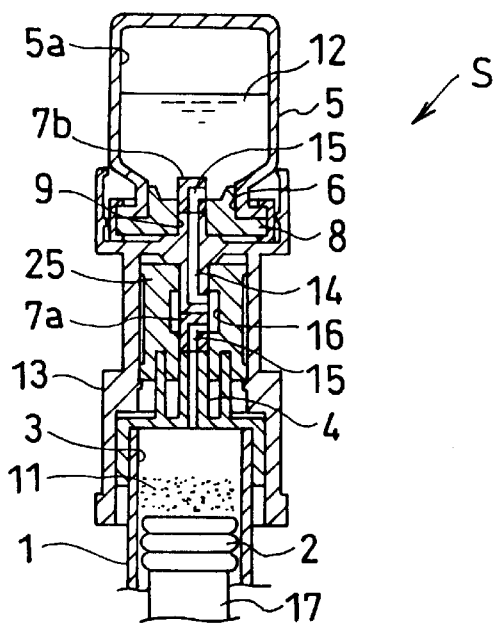
FIG. 5 is a sectional view showing the principal parts of the injector of the modification of the first embodiment during the process of the mixing operation.

FIGS. 4 and 5 show a modification of the first embodiment. FIG. 4 is a sectional view showing principal parts of a dual-chamber type injector while being stored. FIG. 5 is a sectional view showing the principal parts during the process of a mixing operation.

As shown in FIG. 4, this modification attaches, to the needle connecting portion 4, a supporting cylinder 25 by which the first closure member 7a is slidably supported so as to openably cut off communication between an intermediate chamber 16 formed within the supporting cylinder 25 and the drug accommodating chamber 3.

The supporting cylinder 25 is fitted into the connector 13 so as to be slidably movable toward the container chamber 5a. While the injector (S) is being stored, the supporting cylinder 25 is adapted to cut off the communication passage 14 formed in the connector 13 with its inner surface and slidably move so as to communicate the communication passage 14 with the intermediate chamber 16.

Like in the first embodiment, when the hermetically closed container 5 is pushed downward, it moves in proximity to the syringe 1 to displace the supporting cylinder 25, first closure member 7a and second closure member 7b to thereby open the communication passage 14. Thus the injector (S) comes to a state as shown in FIG. 5.

The other construction is the same as that of the first embodiment and the same operation mixes the powder drug 11 with the dissolving liquid 12 and dissolves it therein.

(Second Embodiment)

Figure 6:
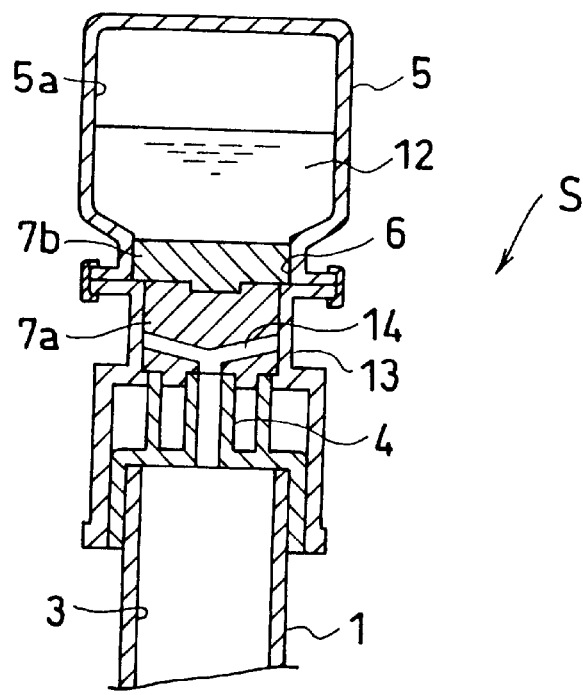
FIG. 6 illustrates a second embodiment of the first invention and corresponds to FIG. 4.
Figure 7:
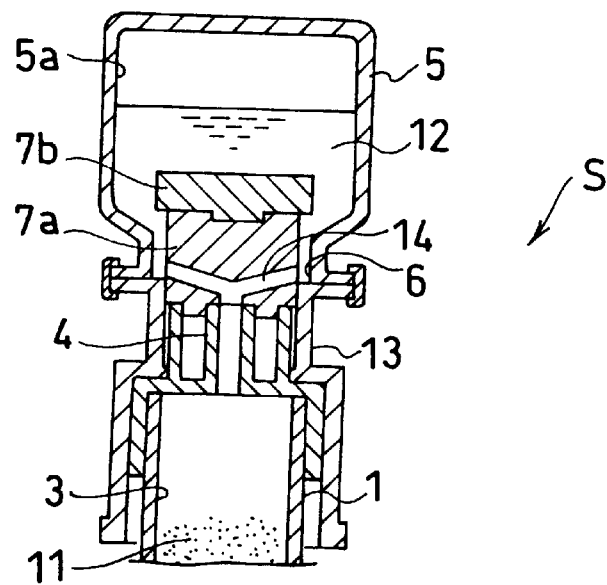
FIG. 7 is a view of the second embodiment corresponding to FIG. 5.

FIGS. 6 and 7 show a second embodiment of the first invention. FIG. 6 is a sectional view showing principal parts of a dual-chamber type injector while being stored. FIG. 7 is a sectional view showing the principal parts during the process of the mixing operation.

As shown in FIG. 6, this second embodiment externally fits a connector 13 housing a first closure member 7a onto a needle connecting portion 4 of a syringe 1. The first closure member 7a is provided with a Y-shaped communication passage 14. This communication passage 14 has one end communicated with an opening of the needle connecting portion 4 and two other ends sealed with an inner surface of the connector 13. In this embodiment, the communication passage is formed in the Y-shape, but it may be formed in any other shape.

The connector 13 is fixed at its upper end to a takeout port 6 of a hermetically closed container 5 in intimate contact therewith. A second closure member 7b is internally fitted into the takeout port 6 so as to hermetically seal a container chamber 5a. This second closure member 7b is fixed to the first closure member 7a with an adhesive.

When the syringe 1 is moved relatively to the container 5, the first and second closure members 7a and 7b are pushed into the container chamber 5a to open the communication passage 14, thereby communicating a drug accommodating chamber 3 with the container chamber 5a as shown in FIG. 7.

Next, a dissolving liquid 12 within the container chamber 5a is made to flow into the drug accommodating chamber 3 through the communication passage 14. After having mixed a powder drug 11 with the dissolving liquid 12 and dissolved it therein, the syringe 1 is separated from the connector 13. At this time, since both of the closure members 7a and 7b are left in the connector 13 and only the syringe 1 is separated, a separately prepared injection needle 10 is attached to the needle connecting portion 4 so as to complete the preparation for drug administration.

Either of the first and second embodiments arranges the first and second closure members 7a and 7b between the drug accommodating chamber 3 and the container chamber 5a and hermetically seals both the chambers 3 and 5a independently with them. Accordingly, for example, even if the container 5 accommodating the dissolving liquid 12 is sterilized with heated vapour, the moisture adsorbed onto the second closure member 7b is unlikely to exert a bad influence on the powder drug 11 within the drug accommodating chamber 3.

However, according to the present invention, if there is no need to consider the moisture adsorbed onto the closure member, as in a case where both components are liquid, only one closure member may be arranged between the drug accommodating chamber and the container chamber.
(Third Embodiment)

Figure 8:
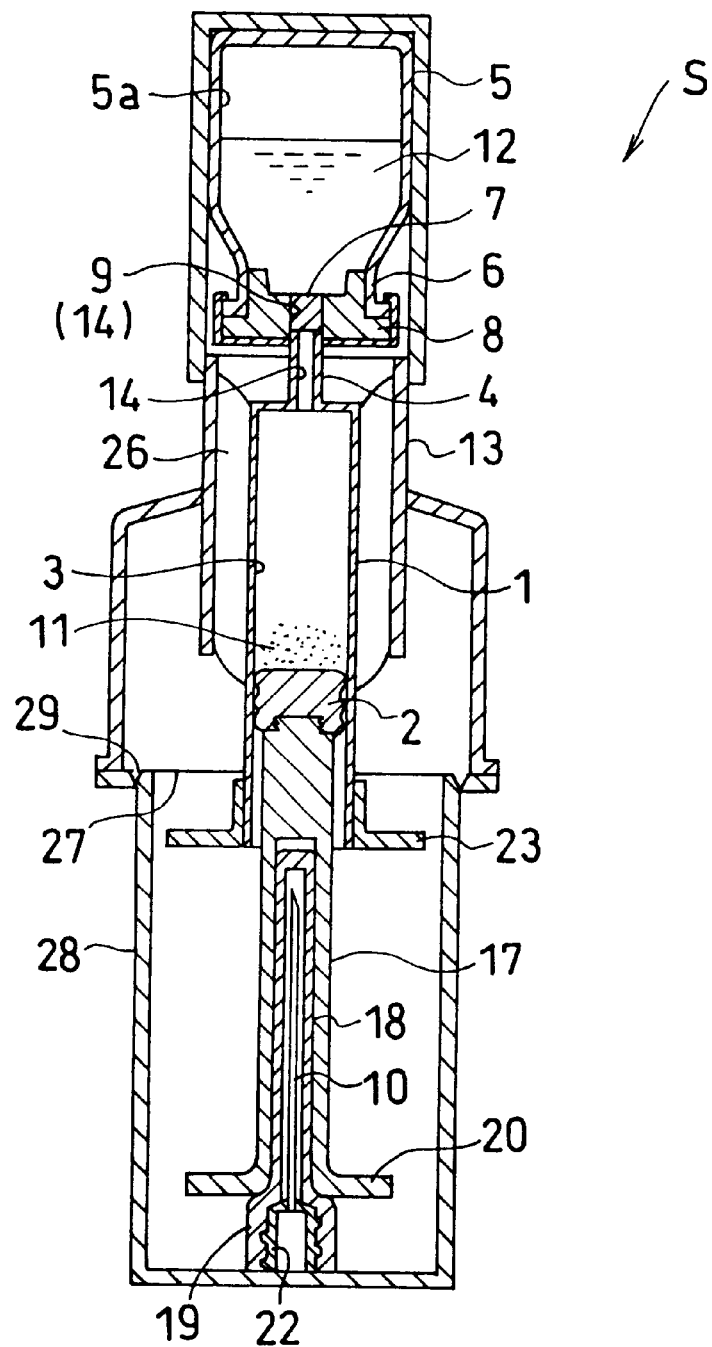
FIG. 8 illustrates a third embodiment of the first invention and corresponds to FIG. 1.
Figure 9:
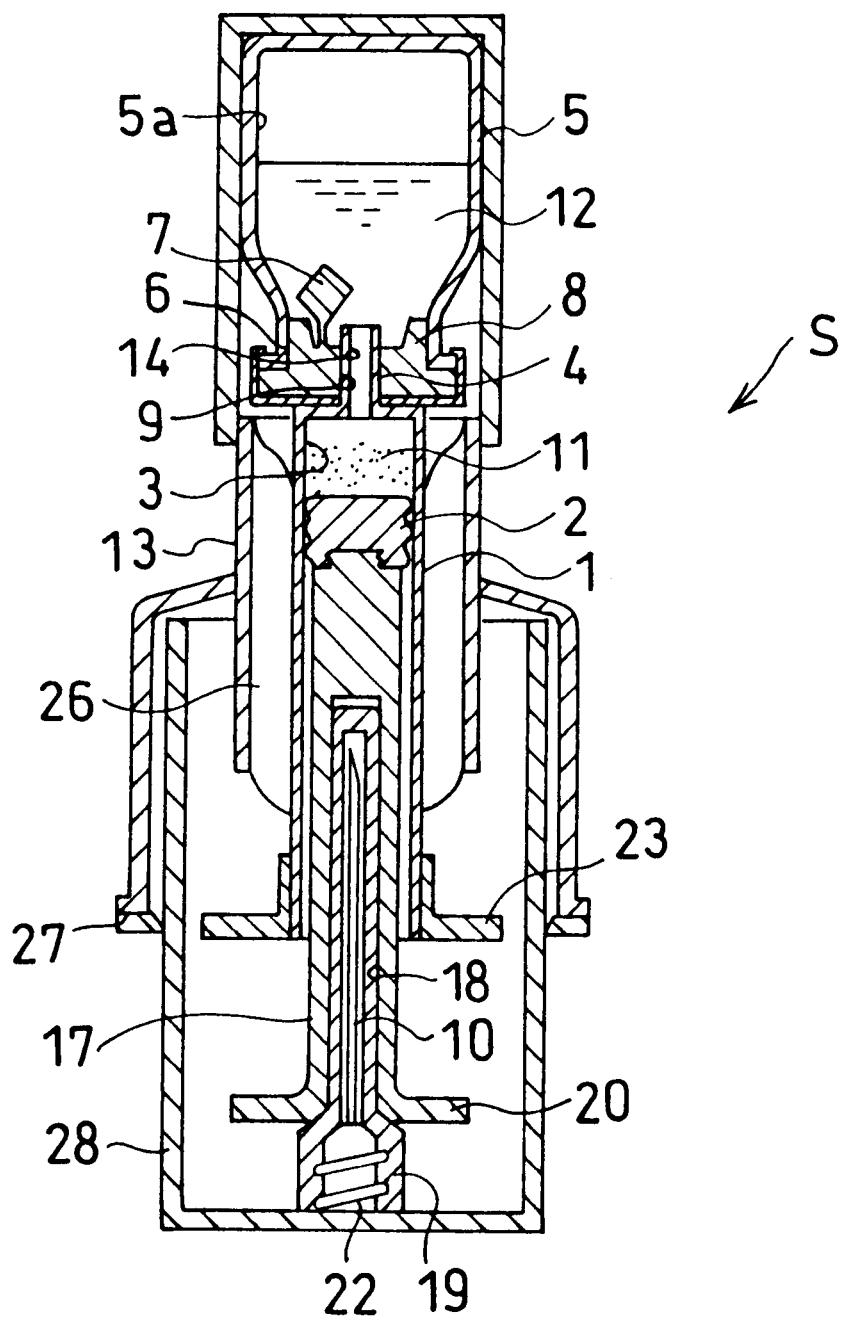
FIG. 9 is a view of the third embodiment and corresponds to FIG. 2.
Figure 10:
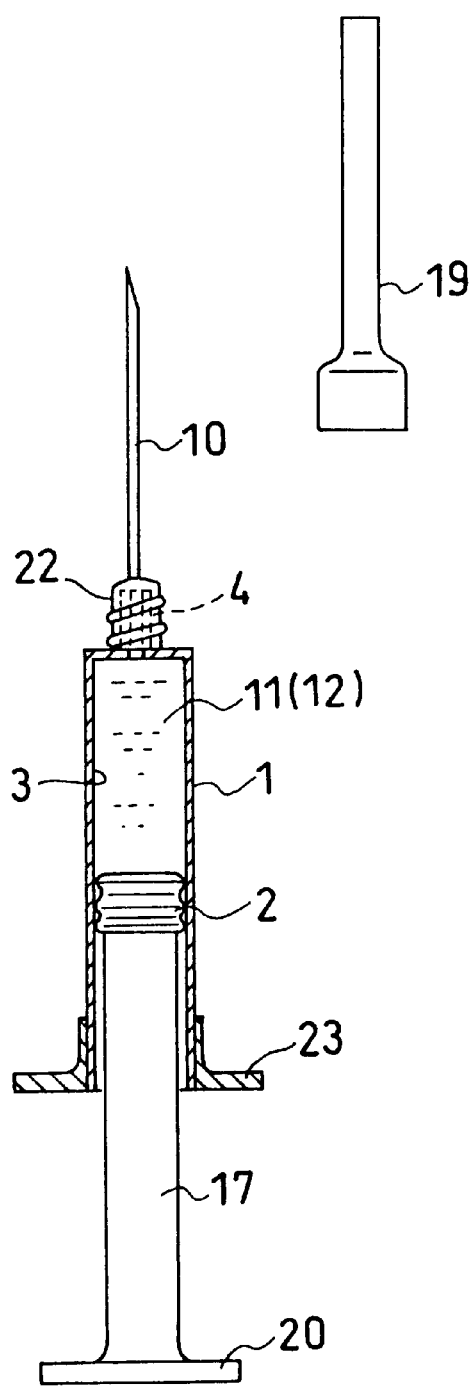
FIG. 10 is a sectional view of a syringe of the third embodiment with an injection needle attached thereto and a protector removed therefrom at the time of administering a drug.

FIGS. 8 to 10 show a third embodiment of the first invention using a single closure member. FIG. 8 is a sectional view of a dual-chamber type injector while being stored. FIG. 9 is a sectional view of the dual-chamber type injector during the process of the mixing operation. FIG. 10 is a sectional view of a syringe with an injection needle attached thereto and a protector removed therefrom at the time of administering a drug.

As shown in FIG. 8, the dual-chamber type injector (S) of the third embodiment attaches a hermetically closed container 5 to a connector 13 in the shape of a bottomed cylinder and supports a syringe 1 by a rib 26 in the connector 13 movably toward the container 5 with a needle connecting portion 4 at a front end of the syringe 1 opposed to a sealing closure 8 hermetically sealing a takeout port 6 of the container 5.

The sealing closure 8 is provided at its mid portion with a through hole 9 so as to slidably fit a closure member 7 therein. The closure member 7 intimately contacts with an open end of the needle connecting portion 4 to hermetically seal a drug accommodating chamber 3 within the syringe 1.

A cover 28 is fixed to a lower opening 27 of the connector 13 so as to hermetically seal the syringe 1 and a piston rod 17. The cover 28 is provided at a peripheral edge of its upper end with a groove 29 similar to the annular easily broken portion of the prior art.

The piston rod 17 accommodates an injection needle 10 covered with a protector 19.

When the connector 13 of the dual-chamber type injector (S) is pushed downward on a desk or the like, the groove 29 of the cover 28 breaks to push up the piston rod 17 together with the cover 28. Consequently, the inner pressure of the drug accommodating chamber 3 increases to move the syringe 1 toward the container 5 and then the needle connecting portion 4 presses the closure member 7 to push it into the container chamber 5a. Thus the injector (S) reaches a communicated state as shown in FIG. 9. Accordingly, in the third embodiment, the through hole 9 and the needle connecting portion 4 compose a communication passage 14.

At this time, a front end of the needle connecting portion 4 slightly invades the container chamber 5a. On the other hand, the closure member 7 is partly connected to an inner surface of the sealing closure 8. Therefore, there is no likelihood that the closure member 7 optionally floats in a dissolving liquid 12 within the container chamber 5a or clogs the opening at the front end of the needle connecting portion 4.

Next, when the pushing force is cancelled, the dissolving liquid 12 flows into the drug accommodating chamber 3 through the communication passage 14 to mix with and dissolve a powder drug 11 within the drug accommodating chamber 3.

Thereafter, the syringe 1 is rid of excessive gas and separated from the connector 13. An injection needle 10 is attached to the needle connecting portion 4. Then, as shown in FIG. 10, the protector 19 is taken away to use the syringe 1 for administering the drug.
(Fourth Embodiment)

Figure 11:
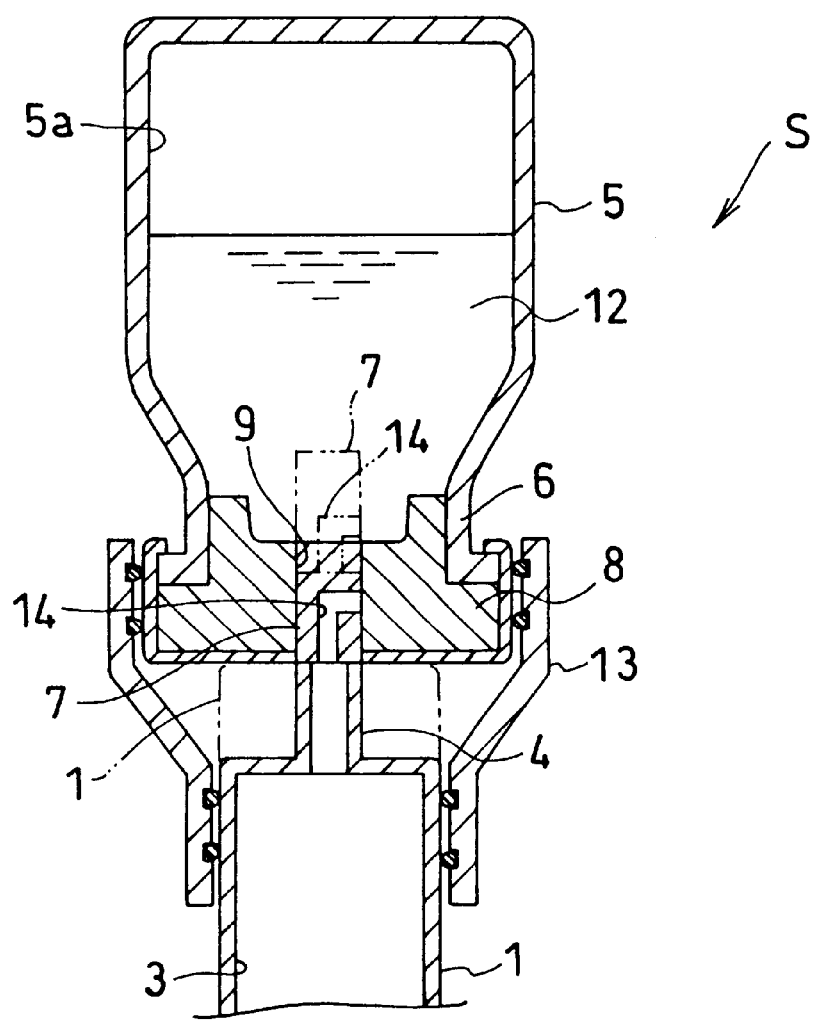
FIG. 11 illustrates a fourth embodiment of the first invention and corresponds to FIG. 4.

FIG. 11 illustrates a fourth embodiment of the first invention and is a sectional view showing principal parts of a dual-chamber type injector which uses a single closure member.

As shown in FIG. 11, the dual-chamber type injector (S) of the fourth embodiment comprises a syringe 1 and a hermetically closed container 5 connected and fixed to each other through a cylindrical connector 13 having its one end diametrically expanded. The syringe 1 is adapted to be movable toward the container 5.

A sealing closure 8 for hermetically sealing a takeout port 6 of the container 5 is provided at its mid portion with the same through hole 9 as that of the third embodiment. A closure member 7 fitted into the through hole 9 is provided with a communication passage 14. The communication passage 14 has its one end opened toward an open end of a needle connecting portion 4 and its other end sealed with an inner surface of the through hole 9.

When the syringe 1 is moved toward the container 5 until it reaches a position indicated by an imaginary line, the closure member 7 is pushed by the needle connecting portion 4 to move into a container chamber 5a and the other end of the communication passage 14 is opened within the container chamber 5a to thereby communicate the container chamber 5a with a drug accommodating chamber 3.
(Fifth Embodiment)

Figure 12:
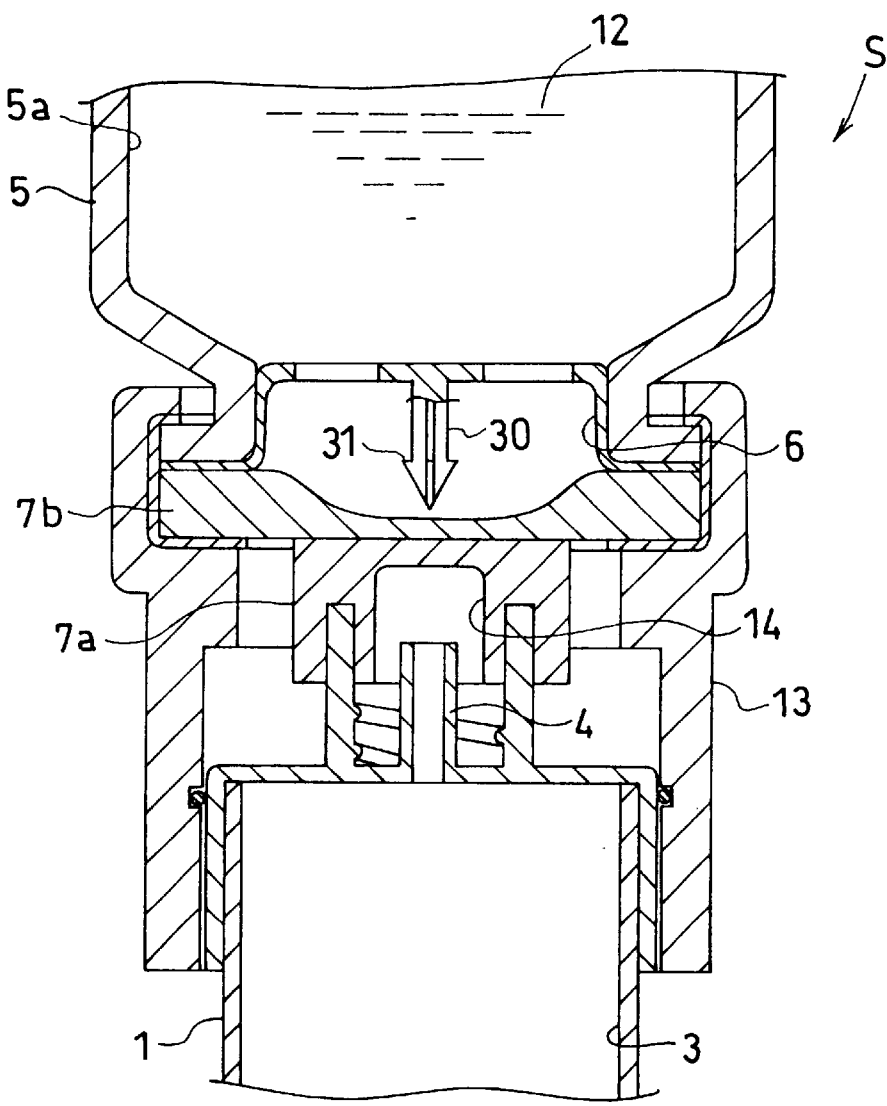
FIG. 12 illustrates a dual-chamber type injector of a fifth embodiment corresponding to a second invention and is a sectional view showing its principal parts.

FIG. 12 illustrates a dual-chamber type injector of a fifth embodiment corresponding to a second invention and is a sectional view showing its principal parts.

As shown in FIG. 12, this fifth embodiment connects a syringe 1 including a drug accommodating chamber 3, hermetically sealed by attaching a first closure member 7a to a needle connecting portion 4, to a hermetically closed container 5 having a takeout port 6, hermetically sealed by a second closure member 7b, through a connector 13. A piercing member 30 is supported by the takeout port 6 with its leading end opposed to the second closure member 7b.

The first closure member 7a is fixed to the second closure member 7b with an adhesive or the like. When the syringe 1 is moved in proximity to the container 5, the second closure member 7b curves to move its mid portion into a container chamber 5a. As a result, the piercing member 30 pierces the second closure member 7b and the first closure member 7a to open a communication passage 14 between the drug accommodating chamber 3 and the container chamber 5a.

In this embodiment, either or both of the above-mentioned closure members may be formed from a sealing member in the shape of a film or the like for the reason of facilitating the piercing operation and so on.

The piercing member 30 is provided on a periphery of its leading end side with an engaging portion 31, so that it is engaged with both of the closure members 7a and 7b by the above piercing. Therefore, when the syringe 1 is separated from the connector 13 after the mixing and dissolving operation, the first closure member 7a is automatically removed from the needle connecting portion 4 to facilitate the attachment of an injection needle.

In the foregoing embodiments, explanation was made as regards a case where the container chamber accommodates a liquid component and the drug accommodating chamber accommodates a solid component. However, needless to say, according to the present invention, the drug accommodating chamber may accommodate a liquid component and the container chamber may accommodate a solid or liquid component.
(Sixth Embodiment)

Figure 13:
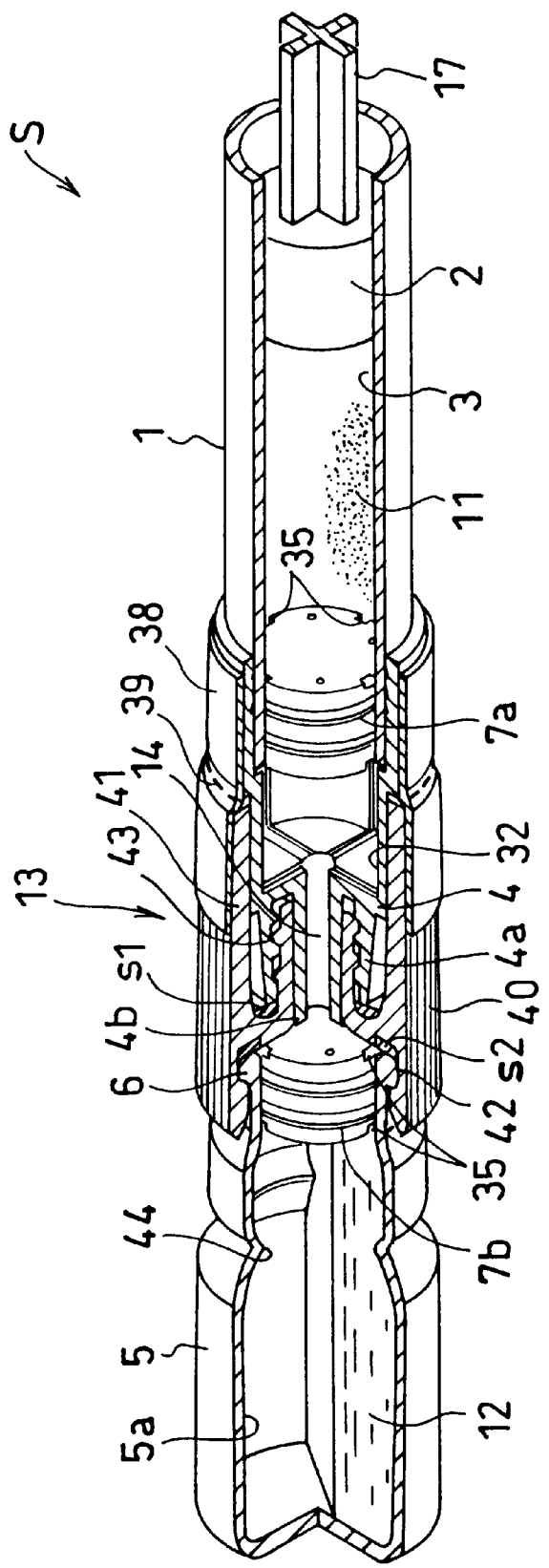
FIG. 13 is a partly broken perspective view showing a dual-chamber type injector and a connector used therefor of a sixth embodiment corresponding to third and fourth inventions.
Figure 14:
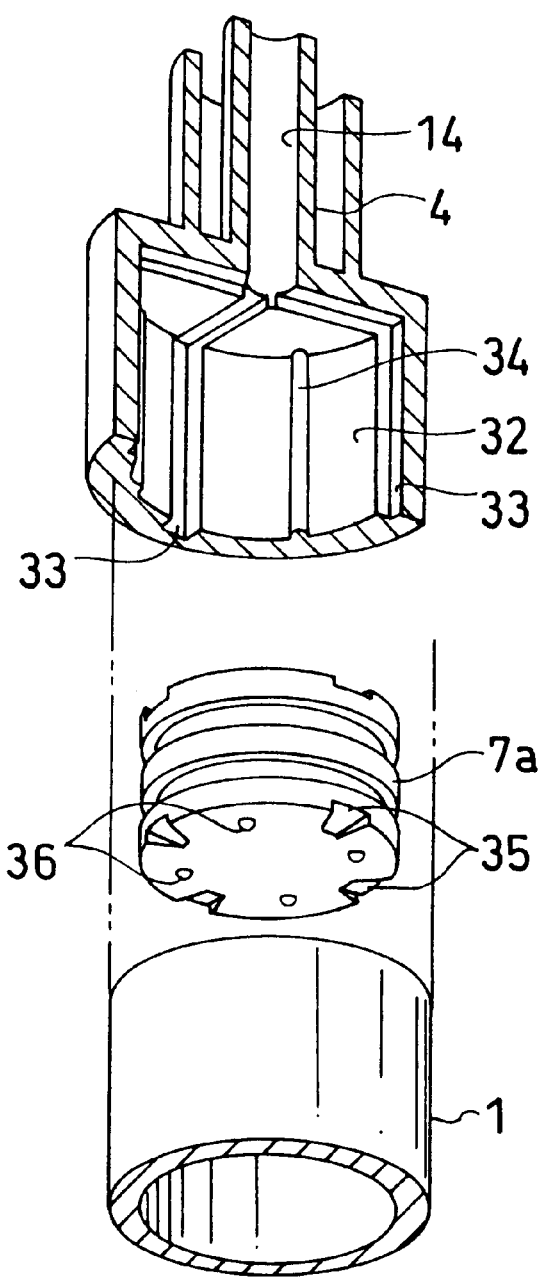
FIG. 14 is a broken perspective view showing the neighborhood of a needle connecting portion of the sixth embodiment.
Figure 15:
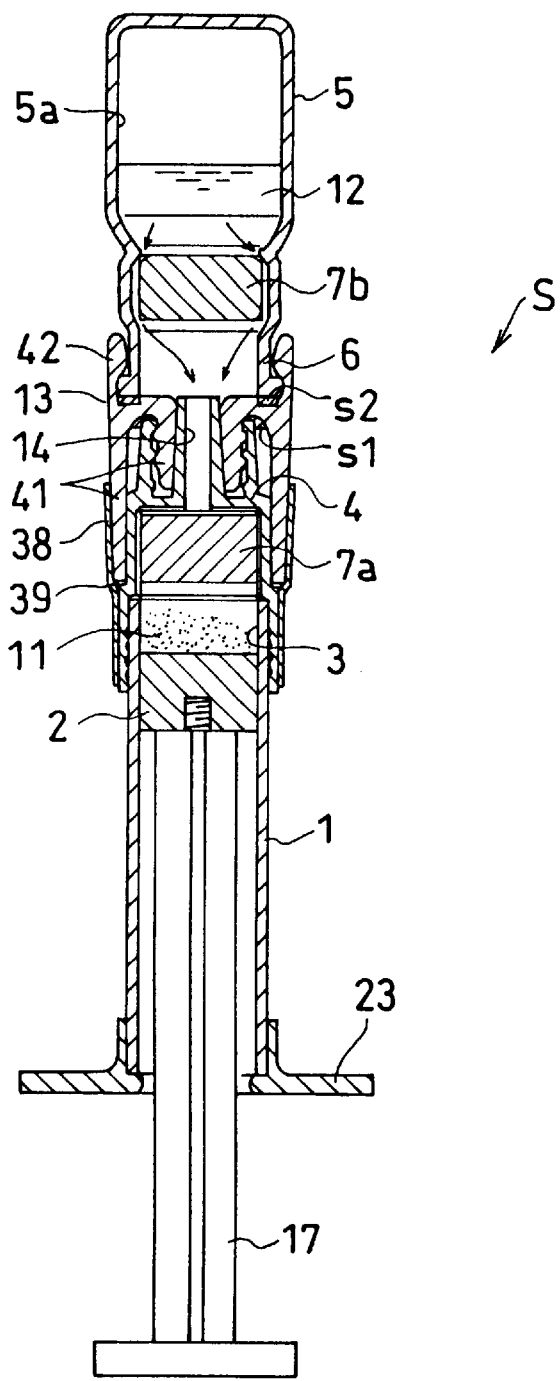
FIG. 15 is a view of the sixth embodiment that corresponds to FIG. 2.
Figure 16:
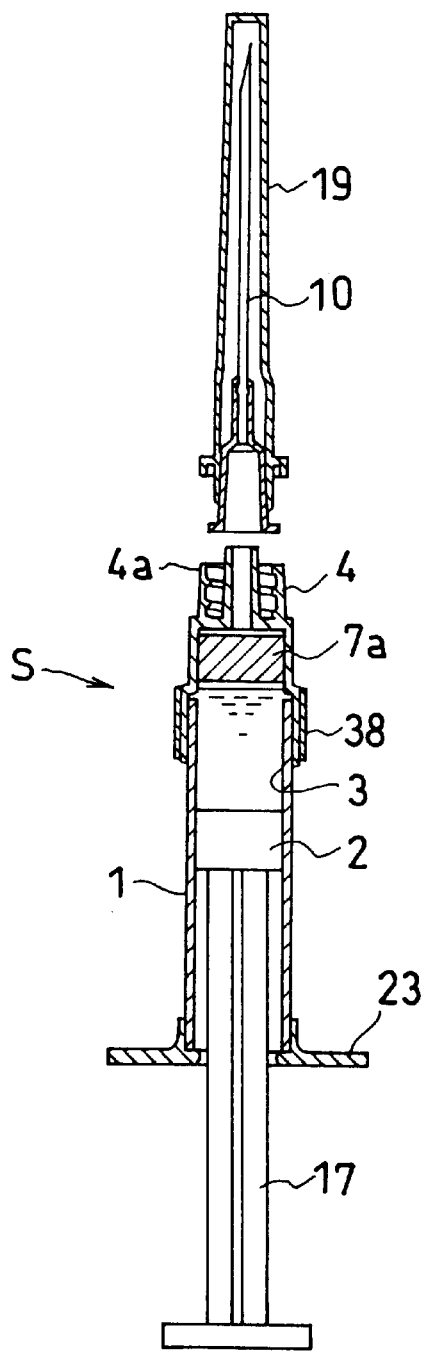
FIG. 16 is a sectional view showing a syringe of the sixth embodiment after the mixing operation.

FIGS. 13 to 16 show a dual-chamber type injector and a connector used therefor of a sixth embodiment corresponding to third and fourth inventions. FIG. 13 is a partly broken perspective view of the injector while being stored. FIG. 14 is a broken perspective view of the neighborhood of a needle connecting portion. FIG. 15 is a sectional view of the injector during the process of the mixing operation. FIG. 16 is a sectional view of a syringe after the mixing operation.

This sixth embodiment forms, between a piston 2 hermetically sealing a rear end side of an interior of a syringe 1 and a first closure member 7a hermetically sealing a front end side thereof, a drug accommodating chamber 3 which accommodates a powder drug 11 of a first component, as shown in FIG. 13.

The syringe 1 is connected and fixed to a hermetically closed container 5 of a vial through a connector 13. The container 5 accommodates a dissolving liquid 12 of a second component with its takeout port 6 hermetically sealed by a second closure member 7b.

Although a piston rod 17 is preliminarily screwed into the piston 2, it may be removed from the piston 2 while the injector is being stored and may be packed together with the syringe 1 and a separately prepared injection needle (not shown) in one set.

The connector 13 comprises a cylindrical body 40 having a syringe fixing portion 41 at its one end and a container fixing portion 42 formed at its other end, respectively. The syringe 1 is separably fixed to the connector 13 by engaging an externally threaded portion 43 formed on the syringe fixing portion 41 with an internally threaded portion 4a for fixing injection needle formed in a needle connecting portion 4. The container 5 is fixed to the connector 13 with the takeout port 6 opposed to an opening 4b at a front end of the needle connecting portion 4 by forcibly fitting a neck portion of the takeout port 6 into the container fixing portion 42.

The cylindrical body 40 is integrally formed with sealing members s1 and s2 obtained by gelatinizing lining agents at a position where the front end of the needle connecting portion 4 butts against the cylindrical body 40 and at a position where the neighborhood of the takeout port 6 of the container 5 butts against the cylindrical body 40, respectively. A space between the needle connecting portion 4 and the takeout port 6 is airtightly shielded from the external space by fixing the syringe 1 and the container 5 to the connector 13.

Needless to say, with the connector of the present invention, either of the sealing members may employ an annular rubber packing or other like sealing member instead of the lining agent.

The syringe 1 is adapted to be separable from the connector 13 by rotating it relatively to the latter. However, while storing it or the like, in order to maintain the above airtightness surely, an adhesive tape 38 is wound over an outer surface of the connector 13 as well as on an outer surface of the needle connecting portion 4 so that the syringe 1 might not rotate unintentionally.

The adhesive tape 38 is provided with perforations and therefore broken along the perforations by rotating the syringe 1 relative to the connector 13. Accordingly, it is easily confirmed whether or not an opening operation has been conducted.

The connector 13 is provided in its outer peripheral surface with a number of concaved grooves for sure holding when rotating the syringe 1.

As shown in FIG. 13, formed between the drug accommodating chamber 3 and a container chamber 5a is a communication passage 14 including an interior of the needle connecting portion 4 and an interior of the takeout port 6 of the container 5.

There is formed in the needle connecting portion 4 a communication chamber 32 having an inner diameter slightly larger than an outer diameter of the first closure member 7a. The communication passage 14 is adapted to open when the first closure member 7a moves to reach an interior of the communication chamber 32.

More specifically, as shown in FIG. 14, the communication chamber 32 has an inner surface provided with vertical grooves 33 and projections 34 so as to secure a communication space around the first closure member 7a therein. However, providing that either of the vertical grooves 33 and the projections 34 are sufficient to secure the communication space, either of them, for example, the projections 34, may be omitted.

Further, the first closure member 7a is provided with communication grooves 35 at a peripheral edge of each of its upper and lower surfaces. In addition, projections 36 are provided on its upper and lower surfaces. Accordingly, even if the first closure member 7a moves to an upper portion or a lower portion of the communication chamber 32, it is unlikely to clog the communication passage 14.

On the other hand, the container chamber 5a within the container 5 is provided with an annular inward projection 44 at a position spaced a little further than a length of the second closure member 7b when from the takeout port 6 as shown in FIG. 13. The annular projection 44 prevents the second closure member 7b, when pushed into the container chamber 5a, from freely moving within the container chamber 5a. The second closure member 7b is also provided with communication grooves 35 in its upper and lower surfaces so that it might not hinder communication after the communication passage 14 has been opened.

Both of the components 11 and 12 are mixed with each other in the dual-chamber type injector (S) by pushing the piston 2 with the piston rod 17.

More specifically, when pushed, the piston 2 increases the inner pressure of the syringe 1 to move the first closure member 7a toward the container 5 until it reaches the communication chamber 32. If the piston 2 is further pushed, gas within the syringe 1 flows out of the front end of the needle connecting portion 4 through an outer peripheral space around the first closure member 7a within the communication chamber 32. Since the space between the needle connecting portion 4 and the takeout port 6 is airtightly shielded from the external space, the pressure of the gas flowing out of the needle connecting portion 4 pushes the second closure member 7b hermetically sealing the takeout port 6 into the container chamber 5a to open the communication passage 14.

Next, as shown in FIG. 15, with the hermetically closed container 5 arranged upward, the piston 2 is pulled back by reducing its pushing force, thereby allowing the dissolving liquid 12 within the container chamber 5a to pass through an outer peripheral space around the second closure member 7b, the interior of the takeout port 6, the interior of the needle connecting portion 4 and the outer peripheral space of the first closure member 7a in order, and then flow into the drug accommodating chamber 3. The powder drug 11 is mixed with and dissolved in the dissolving liquid 12 to prepare a liquid injection.

Thereafter, the syringe 1 is rotated to break the adhesive tape 38 along the perforations 39 and removed from the connector 13. Then, as shown in FIG. 16, a separately prepared injection needle 10 is attached to the needle connecting portion 4, thereby completing the preparation for drug administration.

As a means for preventing the unintentional relative rotation between the syringe 1 and the connector 13, other suitable means can be employed instead of the above-mentioned adhesive tape. For example, a cylindrical shrink film or an annular engaging means 45 as shown in FIG. 17 may be used. The annular engaging member 45 is composed of two semicylindrical bodies 47, 47 connected to each other by a hinge 46. These semicylindrial bodies 47, 47 are adjusted to form a cylindrical body having an inner diameter substantially equal to an outer diameter of the needle connecting portion or the connector by engaging their free ends 48, 48 with each other. The annular engaging member 45 is provided on its inner surface with a number of projections 49, which are adapted to engage with grooves formed in outer surfaces of the needle connecting portion and the connector.

FIG. 18 illustrates a first modification of the sixth embodiment and is an enlarged sectional view showing the neighborhood of the takeout port of the hermetically closed container.

This first modification forms a sealing projection 50 and a posture retaining projection 51 on the outer surface of the second closure member 7b. The second closure member 7b is also provided with a communication hole 52 communicating its outer surface with a portion between both the projections 50 and 51.

When opening the communication passage 14, the pressure of a fluid flowed out of the needle connecting portion 4 pushes the second closure member 7b into the container chamber 5a to result in taking the sealing projection 50 away from the inner surface of the takeout port 6 and opening the communication passage 14. With the communication passage 14 opened, the posture retaining projection 51 is still supported by the inner surface of the takeout port 6, so that the second closure member 7b does not freely move within the container chamber 5a. Further, the sealing projection 50 being formed slantingly around the second closure member 7b as shown in FIG. 18, even if the second closure member 7b slightly moves toward the needle connecting portion 4 when the liquid returns from the container camber 5a into the syringe 1, the sealing projection 50 does not enter the takeout port 6 in its entirety and therefore does not hinder the communication after the communication passage has been opened.

Figure 19:
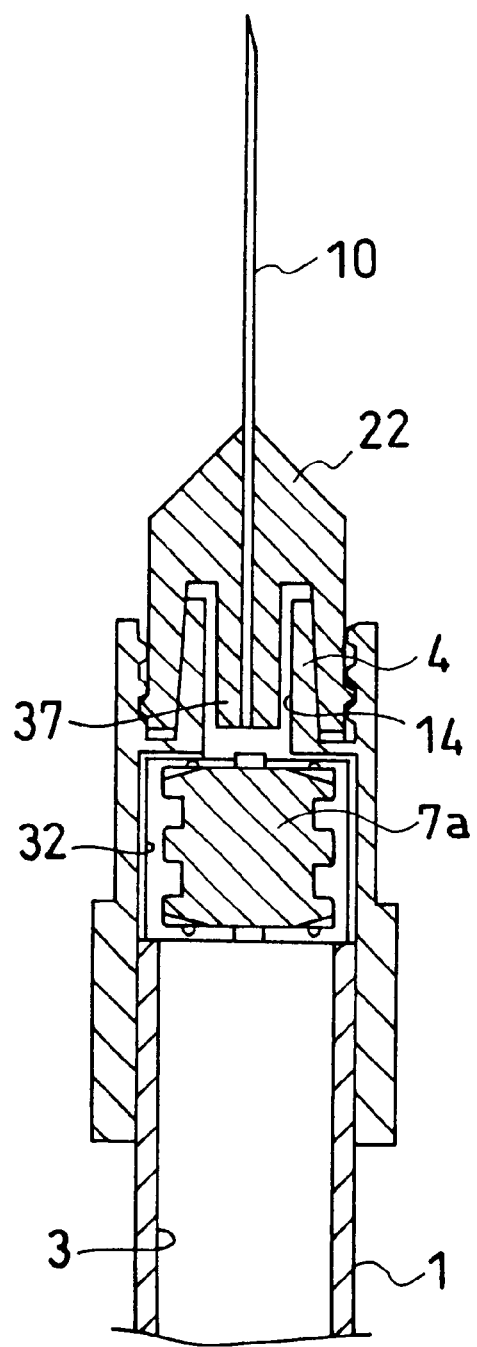
FIG. 19 illustrates a second modification of the sixth embodiment and is a sectional view showing the vicinity of an injection needle ready for drug administration.

The dual-chamber type injector according to the present invention may enlarge the inner diameter of the needle connecting portion 4 in a second modification of the sixth embodiment shown in FIG. 19 to more smoothly move the liquid component or surely prevent the powder component from clogging the communication passage so as to mix both components more easily.

In a case where the inner diameter of the needle connecting portion 4 is enlarged as above, it is preferable to construct a hub 22 so that a rear end 37 of an injection needle 10 projects into the needle connecting portion 4 as shown in FIG. 19 in order to reduce the amount of the injection liquid residing within the needle connecting portion 4 when administering the drug.

(Seventh Embodiment)

Figure 20:
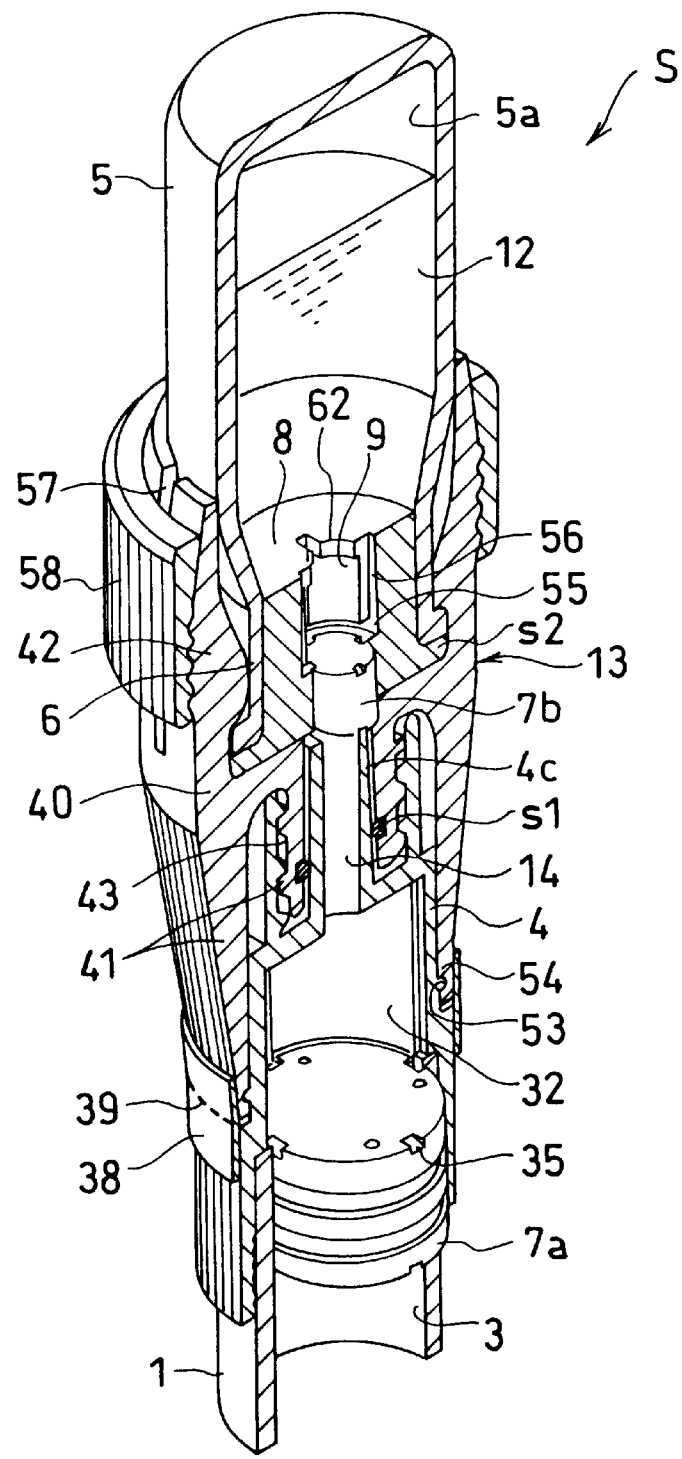
FIG. 20 is a broken perspective view showing the neighborhood of a connector of a seventh embodiment corresponding to the third and fourth inventions.
Figure 21:
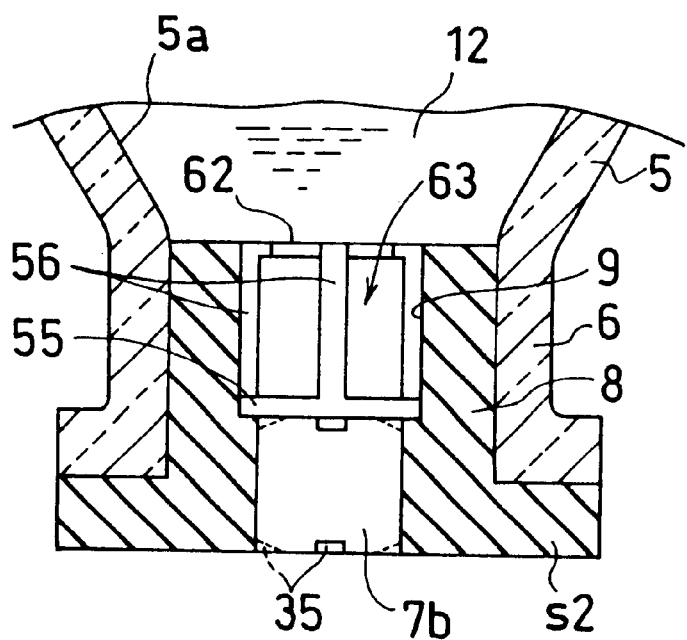
FIG. 21 is a sectional view showing the neighborhood of a takeout port of a hermetically closed container of the seventh embodiment.
Figure 22:
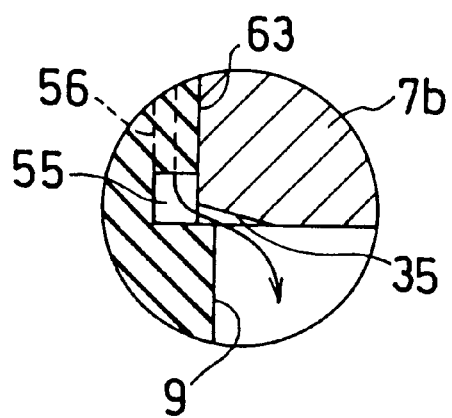
FIG. 22 is a partly enlarged view showing a second closure member of the seventh embodiment.

FIGS. 20 to 22 show a seventh embodiment corresponding to the third and fourth inventions. FIG. 20 is a broken perspective view of the neighborhood of a connector. FIG. 21 is a sectional view of the neighborhood of a takeout port of a hermetically closed container. FIG. 22 is a partly enlarged view of a second closure member.

This seventh embodiment brings an O-ring (s1) attached to an inner surface of a connector 13 into butting contact with an outer surface of a nozzle portion 4c of a needle connecting portion 4. The nozzle portion 4c is tapered in its outer surface, so that the O-ring s1 surely seals a space between the connector 13 and the needle connecting portion 4 by screwing the needle connecting portion 4 into a threaded portion 43 of a syringe fixing portion 41.

A cylindrical body 40 of the connector 13 has an inner surface provided with a first engaging portion 53 comprising an annular groove and the needle connecting portion 4 has an outer surface provided with a second engaging portion 54 comprising an annular projection. Both the engaging portions 53 and 54 engage with each other at the end of the foregoing screw-thread engagement so as not to unintentionally loosen the fixing connection between the syringe 1 and the connector 13. This construction for preventing the loosening may be formed from an engaging portion comprising a concave portion provided in a thread ridge and a convex portion provided on a thread groove in the vicinity of a terminal end of the threaded portion in a pair.

From the aspect of preventing loosening, it is sufficient to engage both of the engaging portions 53 and 54 with each other, and therefore the adhesive tape used in the sixth embodiment may be omitted. However, in order to easily confirm that the opening operation was conducted, an adhesive tape 38 is wound over the syringe 1 and the connector 13 like in the sixth embodiment.

Providing that the syringe can be surely fixed to the connector only through engaging both of the engaging portions 53 and 54 with each other, the threaded portion 43 of the syringe fixing portion 41 may be omitted.

On the other hand, a rubber closure 8 is disposed in a takeout port 6 of a hermetically closed container 5 and is provided at its mid portion with a through hole 9, in which a second closure member 7b, made of a material that is relatively hard but smooth on its surface, such as hard plastic, ceramic, glass or the like, is arranged to be slidably movable and so as to hermetically seal the takeout port 6. A flange portion of the rubber closure 8 also serves as a sealing member s2 for sealing a space between the container 5 and the connector 13.

The through hole 9 has an inner surface provided with an annular groove 55 and vertical grooves 56 on a side nearer to a container chamber 5a than to the second closure member 7b. Thus when the second closure member 7b moves toward the container chamber 5a, the container chamber 5a is communicated with a communication passage 14 through the grooves 55 and 56.

More specifically, the pressure of a fluid flowing out of a front end of the needle connecting portion 4 pushes the second closure member 7b to move it into the container chamber 5a. As shown in FIGS. 20 and 21, the through hole 9 is provided on its side nearer to the container 5 with a closure member accommodating space 63 longer than the second closure member 7b. The pushed second closure member 7b invades the space 63. When communication grooves 35 formed at an outer end of the second closure member 7b are communicated with the annular groove 55 formed in the inner surface of the space 63, the fluid passes through the communication grooves 35, annular groove 55 and vertical grooves 56, and then flows into the container chamber 5a. Accordingly, the pushing force applied on the second closure member 7b by the fluid rapidly decreases. However, at this time the second closure member 7b has mostly invaded the closure member accommodating space 63 and therefore is completely pushed thereinto by a restitutive force of the surrounding rubber closure 8. Provided at an end of the closure member accommodating space 63 are engaging projections 62, which prevent the second closure member 7b, invaded into the space 63, from entering the container chamber 5a.

When the second component 12 within the container chamber 5a flows into the syringe 1 after having communicated the communication passage 14 with the container chamber 5a, the second closure member 7b tends to move toward the syringe 1 upon receipt of the liquid pressure. However, as shown in FIG. 22, the portion of the through hole 9 where the second closure member 7b was originally attached has been narrowed because the second closure member 7b came out. Therefore, there is no probability that the second closure member 7b returns to the original position. Should the second closure member 7b be pushed back toward an outer end side of the closure member accommodating space 63, the communication grooves 35 being formed at the ends of the second closure member 7b, the communication between the container chamber 5a and the communication passage 14 can be secured through the communication grooves 35, annular groove 55 and vertical grooves 56.

A container fixing portion 42 of the connector 13 is extended to a position where it contacts with a barrel portion of the container 5 and is provided on its periphery with a plurality of slits 57 so as to be able to diametrically enlarge. Consequently, it can surely fix the container 5 by screwing a fastening ring 58 thereto. The fastening ring 58 may be attached by striking instead of screwing.

A first closure member 7a and the other construction are the same as those of the sixth embodiment and also the communicating operation or the like is conducted substantially in the same manner, explanation for which is therefore omitted.

(Eighth Embodiment)

Figure 23:
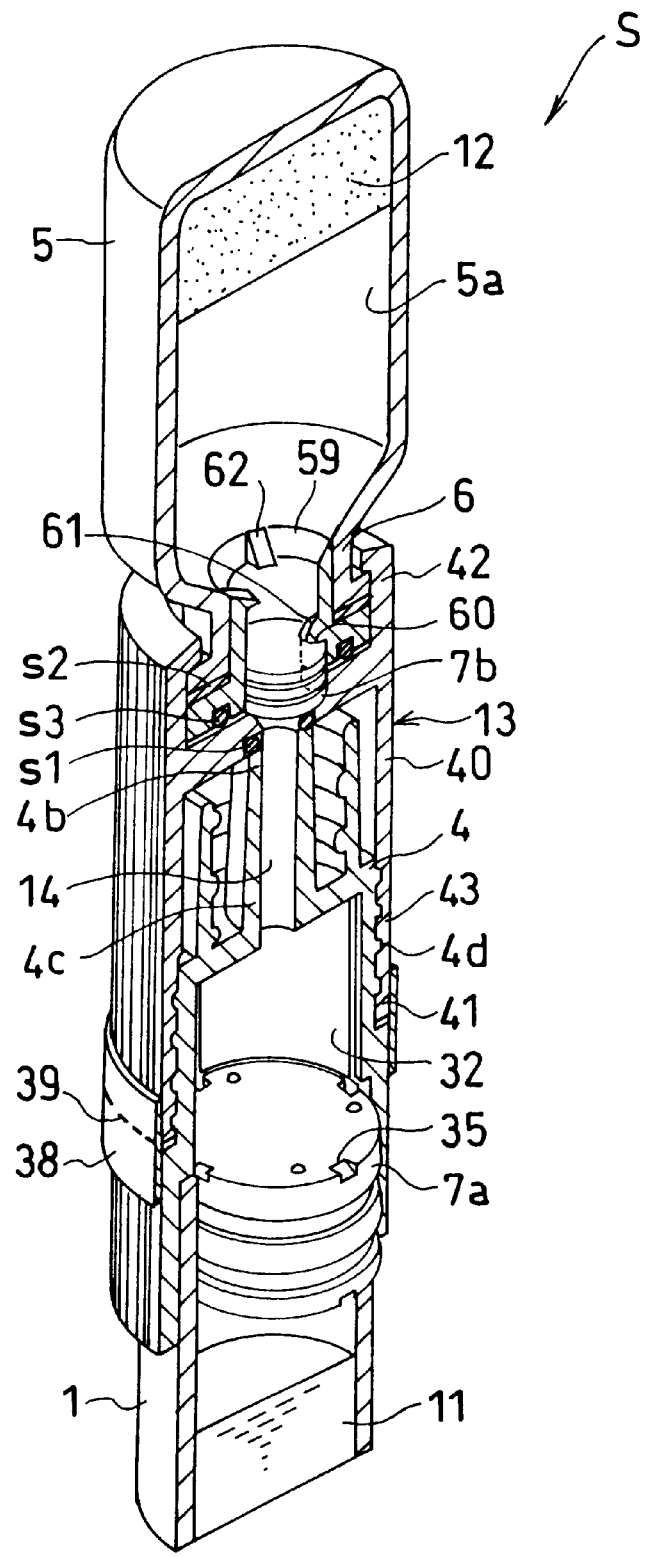
FIG. 23 illustrates an eighth embodiment corresponding to the third and fourth inventions and corresponds to FIG. 20.

FIG. 23 illustrates an eighth embodiment corresponding to the third and fourth inventions and is a broken perspective view showing the neighborhood of a connector.

This eighth embodiment forms an externally threaded portion 4d on an outer surface of a needle connecting portion 4 and fixes a syringe 1 to a connector 13 by engaging the threaded portion 4d with an internally threaded portion 43 formed in a syringe fixing portion 41 of the connector 13.

Further, an O-ring s1 is arranged in butting contact with the periphery of an opening 4b at a front end of the needle connecting portion 4 to thereby extremely reduce the residual amount of liquid between a communication passage 14 and the O-ring s1, a sealing member, and prevent the liquid from splashing and leaking out to the periphery of a nozzle portion 4c.

This eighth embodiment accommodates within a container chamber 5a of a hermetically closed container 5 a solid agent 12 obtained by freeze drying or the like as a second component, unlike the foregoing respective embodiments, and therefore accommodates within a drug accommodating chamber 3 of the syringe 1 a dissolving liquid 11 as a first component. However, needless to say, this eighth embodiment may also accommodate a liquid component within the container chamber 5a like the above-mentioned respective embodiments.

Attached to a takeout port 6 of the container 5 is a plastic member 59 for supporting a closure member. A second closure member 7b is slidably movable within the supporting member 59 to hermetically seal the takeout port 6.

An annular rubber packing s2 is arranged between the supporting member 59 and a flange portion of the takeout port 6 and an O-ring s3 is positioned between the supporting member 59 and the connector 13, thereby airtightly shielding a space between the takeout port 6 and the needle connecting portion 4 from the external space.

The second closure member 7b has a peripheral surface provided with a vertical groove 60, which is sealed by fitting itself onto a projection 61 formed on an inner surface of the supporting member 59. When the second closure member 7b is pushed into the container chamber 5a to be displaced, the vertical groove 60 is separated from the projection 61 and communicates the container chamber 5a with the communication passage 14.

Provided at an inner end of the supporting member 59 are engaging projections 62 to prevent the second closure member 7b from moving freely within the container chamber 5a.

Further, for example, like a modification of the second closure member as shown in FIG. 24, the second closure member 7b has an inner end provided with inclined surfaces, which butt against the engaging projections 62 to rotate the second closure member 7b when the second closure member 7b is pushed in and thereby position the vertical groove 60 offset with respect to the projection 61 in a peripheral direction. As such, it is preferable to construct the second closure member 7b so that the projection 61 is unlikely to clog the vertical groove 60 when returning the liquid drug from the container chamber 5a to the drug accommodating chamber 3.

(Ninth Embodiment)

Figure 25:
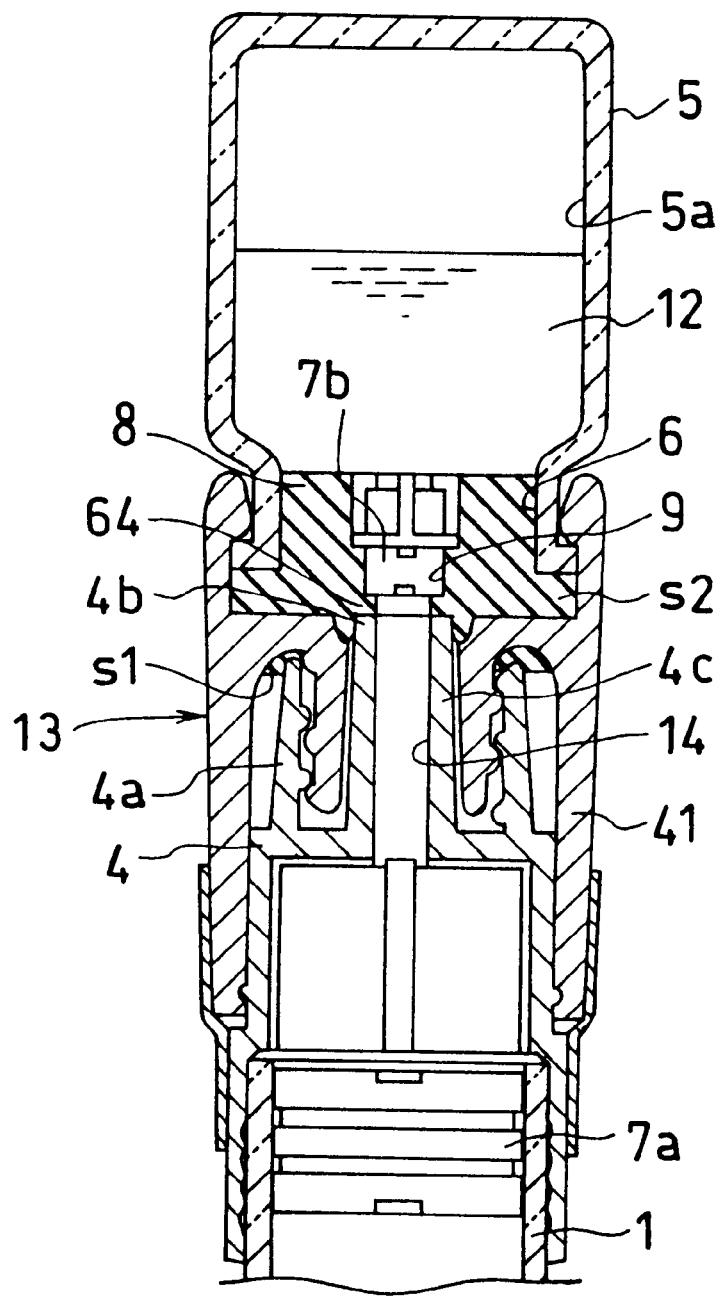
FIG. 25 illustrates a dual-chamber type injector of a ninth embodiment corresponding to the third and fourth inventions and is a vertical sectional view of the neighborhood of a connector.

FIG. 25 illustrates a dual-chamber type injector of a ninth embodiment corresponding to the third and fourth inventions and is a vertical sectional view of the neighborhood of a connector.

This ninth embodiment provides on a syringe fixing portion 41 of a connector 13 the same sealing member s1 obtained by gelatinizing a lining agent as that of the sixth embodiment at a position where an injection needle fixing threaded portion 4a of a needle connecting portion 4 butts at its front end against the syringe fixing portion 41. Meanwhile, a takeout port 6 of a hermetically closed container 5 is hermetically sealed by the same rubber closure 8 having a second closure member 7b arranged in a through hole 9 provided at its mid portion as that of the seventh embodiment. Additionally, the ninth embodiment is identical to the seventh embodiment in that the flange portion of this rubber closure 8 also serves as a sealing member s2 between the container 5 and the connector 13.

This ninth embodiment brings a peripheral edge of an opening 4b at a front end of the needle connecting portion 4 into butting contact with the rubber closure 8, thereby liquid-tightly sealing a communication passage 14 from the external space, unlike the seventh embodiment. Accordingly, the above sealing member s1 keeps a space between the threaded portion 4a and a nozzle portion 4c of the needle connecting portion 4 sterile until the syringe 1 is separated from the connector 13. Besides, the rubber closure 8 inhibits a dissolving liquid 12 or the like from leaking out of the communication passage 14.

As shown in FIG. 25, the through hole 9 formed at the mid portion of the rubber closure 8 is provided on its side nearer to the syringe 1 than to the second closure member 7b, namely on an outer side of a container chamber 5a with an annular projection 64. This annular projection 64 prevents the second closure member 7b from jumping out of the through hole 9 before the container 5 is connected and fixed to the syringe 1 through the connector 13.

(Tenth Embodiment)

FIG. 26 illustrates a dual-chamber type injector of a tenth embodiment corresponding to the third and fourth inventions and is a vertical sectional view of the neighborhood of a connector.

In the sixth to ninth embodiments, explanation was made as to a case where a needle connecting portion has an injection needle fixing threaded portion. In this tenth embodiment, the needle connecting portion 4 has no injection needle fixing threaded portion.

A syringe 1 has a connector 13 fixed thereto by screwing it onto a threaded portion 4d formed on an outer surface of the needle connecting portion 4 and airtightly shields an interior of a nozzle portion 4c from the external surface by bringing a rubber packing s1 disposed on a syringe fixing portion 41 into butting contact with the periphery of the nozzle portion 4c of the needle connecting portion 4.

A container fixing portion 42 of the connector 13 is provided with a pushing projection 65 so as to surely hold a flange portion of a rubber closure 8 serving as a sealing member s2. The other construction is the same as that of the ninth embodiment and accordingly explanation therefor is omitted.

(Eleventh Embodiment)

Figure 27:
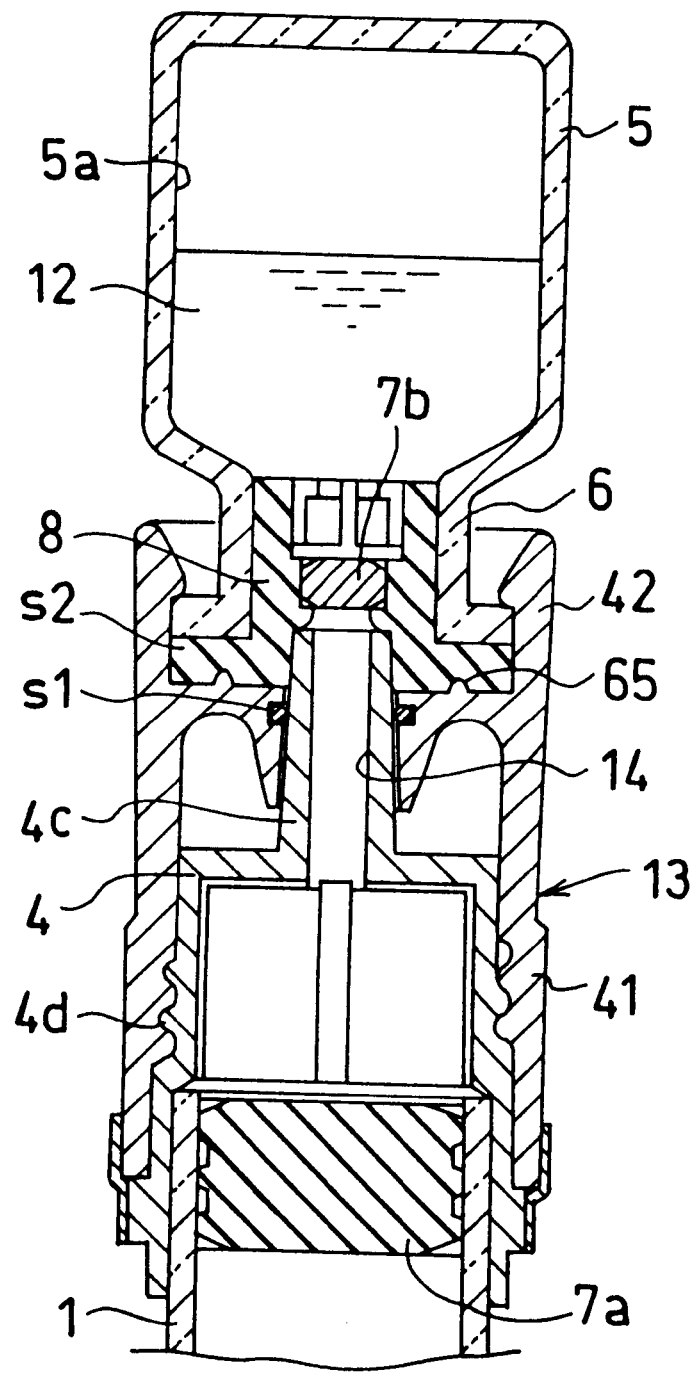
FIG. 27 illustrates a dual-chamber type injector of an eleventh embodiment corresponding to the third and fourth inventions and is a vertical sectional view showing the neighborhood of a connector.

FIG. 27 illustrates a dual-chamber type injector of an eleventh embodiment corresponding to the third and fourth inventions and is a vertical sectional view showing the neighborhood of a connector.

This eleventh embodiment employs an O-ring s1 instead of the rubber packing of the tenth embodiment and airtightly shields a communication passage 14 with an outer surface of a nozzle portion 4c from the external space. The other construction is the same as that of the tenth embodiment and accordingly explanation therefor is omitted.

(Twelfth Embodiment)

Figure 28:
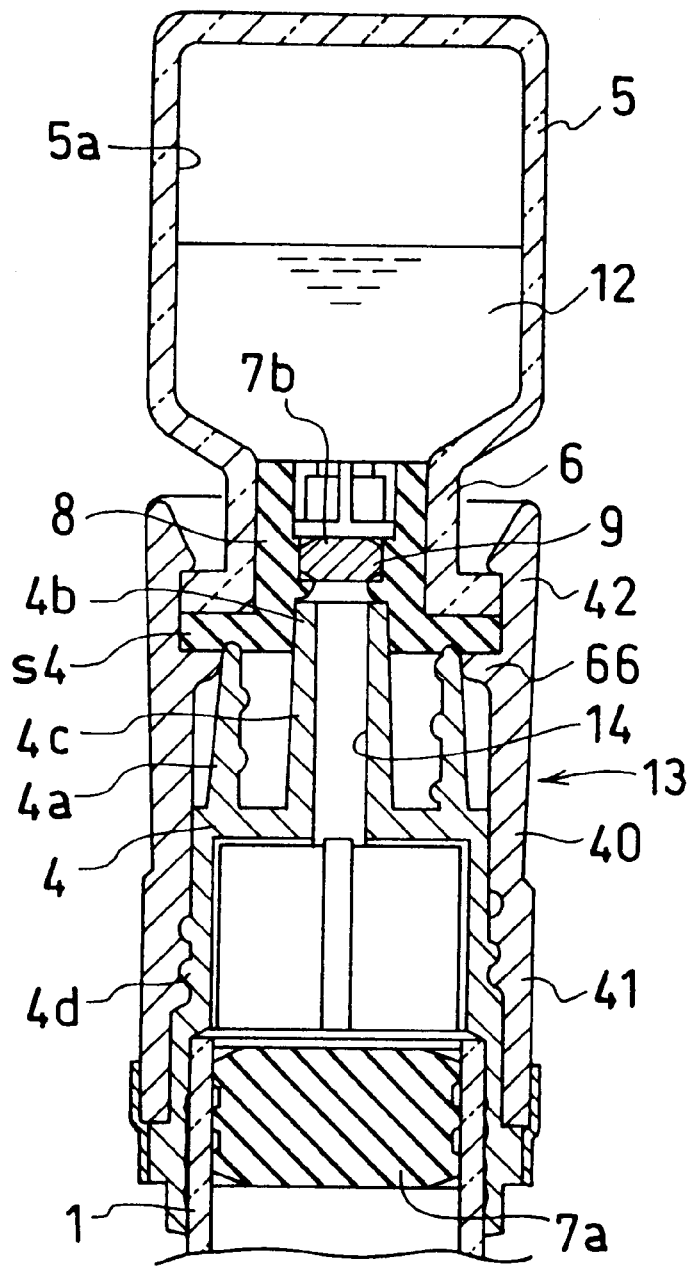
FIG. 28 illustrates a dual-chamber type injector of a twelfth embodiment corresponding to third and fifth inventions and is a vertical sectional view showing the neighborhood of a connector.

FIG. 28 illustrates a dual-chamber type injector of a twelfth embodiment corresponding to the third and fifth inventions and is a vertical sectional view of the neighborhood of a connector.

This twelfth embodiment connects and fixes a syringe 1 to a hermetically closed container 5 through a connector 13 like the sixth to eleventh embodiments. More specifically, the connector 13 comprises a cylindrical body 40 provided with a syringe fixing portion 41 and a container fixing portion 42. A needle connecting portion 4 of the syringe 1 is separably fixed to the syringe fixing portion 41 and a takeout port 6 of the container 5 is secured to the container fixing portion 42 opposite to an opening 4b at a front end of the needle connecting portion 4.

The takeout port 6 is hermetically sealed by the same rubber closure 8 having a second closure member 7b arranged in a through hole 9 provided at its mid portion as that of the seventh embodiment. But this twelfth embodiment differs from the seventh embodiment in that a flange portion of this rubber closure 8 serves as a sealing member s4 between the needle connecting portion 4 and the container 5. More specifically, when the connector 13 is screwed and fixed onto a threaded portion 4d formed on an outer surface of the needle connecting portion 4, an injection needle fixing threaded portion 4a is pushed at its front end to the sealing member s4, the flange portion of the rubber closure 8, to thereby airtightly shield a space between the needle connecting portion 4 inward of the threaded portion 4a and the takeout port 6 from the external space.

The cylindrical body 40 of the connector 13 has an inner surface provided with an annular supporting projection 66, which surely pushes the sealing member s4, the flange portion of the rubber closure 8, to the takeout port 6 of the container 5 and can support a front end side of the needle connecting portion 4 stably.

A nozzle portion 4c of the needle connecting portion 4 has a front end projected into the through hole 9 formed in the rubber closure 8 to liquid-tightly shield a peripheral edge of an opening 4b at its front end from the external space and thereby prevent the leakage of the dissolving liquid 12 or the like.

The other construction is the same as that of the seventh or ninth embodiment and accordingly explanation therefor is omitted.

(Thirteenth Embodiment)

Figure 29:
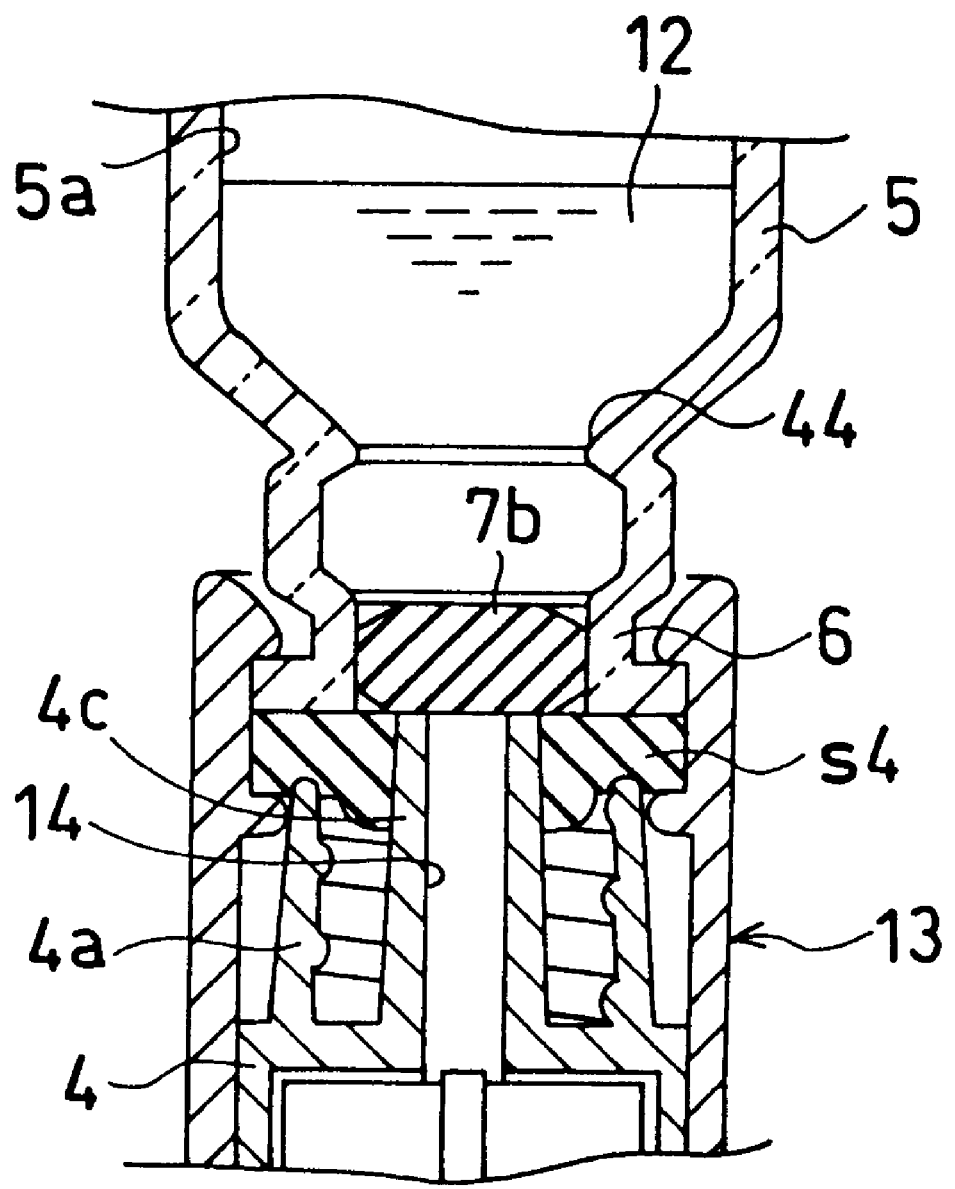
FIG. 29 illustrates a dual-chamber type injector of a thirteenth embodiment corresponding to the third and fifth inventions and is a vertical sectional view showing the neighborhood of a takeout port of a hermetically closed container.

FIG. 29 illustrates a dual-chamber type injector of a thirteenth embodiment corresponding to the third and fifth inventions and is a vertical sectional view showing the neighborhood of a takeout port of a hermetically closed container.

This thirteenth embodiment hermetically seals a takeout port 6 only by a second closure member 7b instead of the rubber closure having the second closure member in the twelfth embodiment. And like the sixth embodiment, it forms an annular inward projection 44 in a container chamber 5a of the container 5 so as to be able to confine the movement of the second closure member 7b pushed into the container chamber 5a.

The takeout port 6 arranges on its periphery an annular rubber packing s4, which is surely pushed to the periphery of the takeout port 6 by a connector 13. When a needle connecting portion 4 is connected and fixed to the container 5, an injection needle fixing threaded portion 4a is pushed at its front end to the rubber packing s4 to thereby airtightly shield a space between the needle connecting portion 4 inward of the threaded portion 4a and the takeout port 6 from the external space. The other construction is the same as that of the twelfth embodiment.

(Fourteenth Embodiment)

Figure 30:
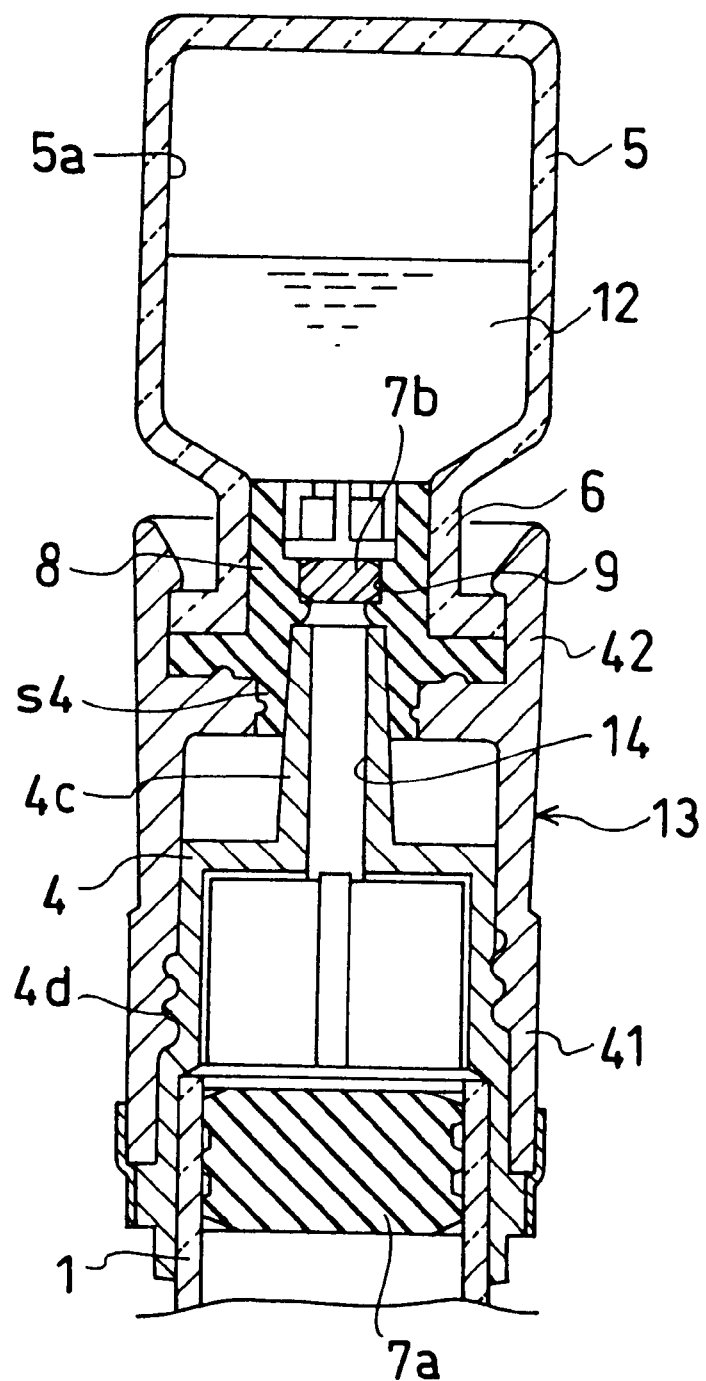
FIG. 30 illustrates a dual-chamber type injector of a fourteenth embodiment corresponding to the third and fifth inventions and is a vertical sectional view showing the neighborhood of a connector.

FIG. 30 illustrates a dual-chamber type injector of a fourteenth embodiment corresponding to the third and fifth inventions and is a vertical sectional view showing the neighborhood of a connector.

In the fourteenth embodiment, a needle connecting portion 4 is provided with no injection needle fixing threaded portion, unlike the twelfth embodiment. Therefore, a rubber closure 8 attached to a takeout port 6 of a hermetically closed container 5 is provided with an annular sealing portion s4 extending therefrom. A nozzle portion 4c of the needle connecting portion 4 is projected into the sealing portion s4 to thereby airtightly shield a space between the needle connecting portion 4 and the takeout port 6 from the external space. The other construction is the same as that of the twelfth embodiment.

(Fifteenth Embodiment)

Figure 31:
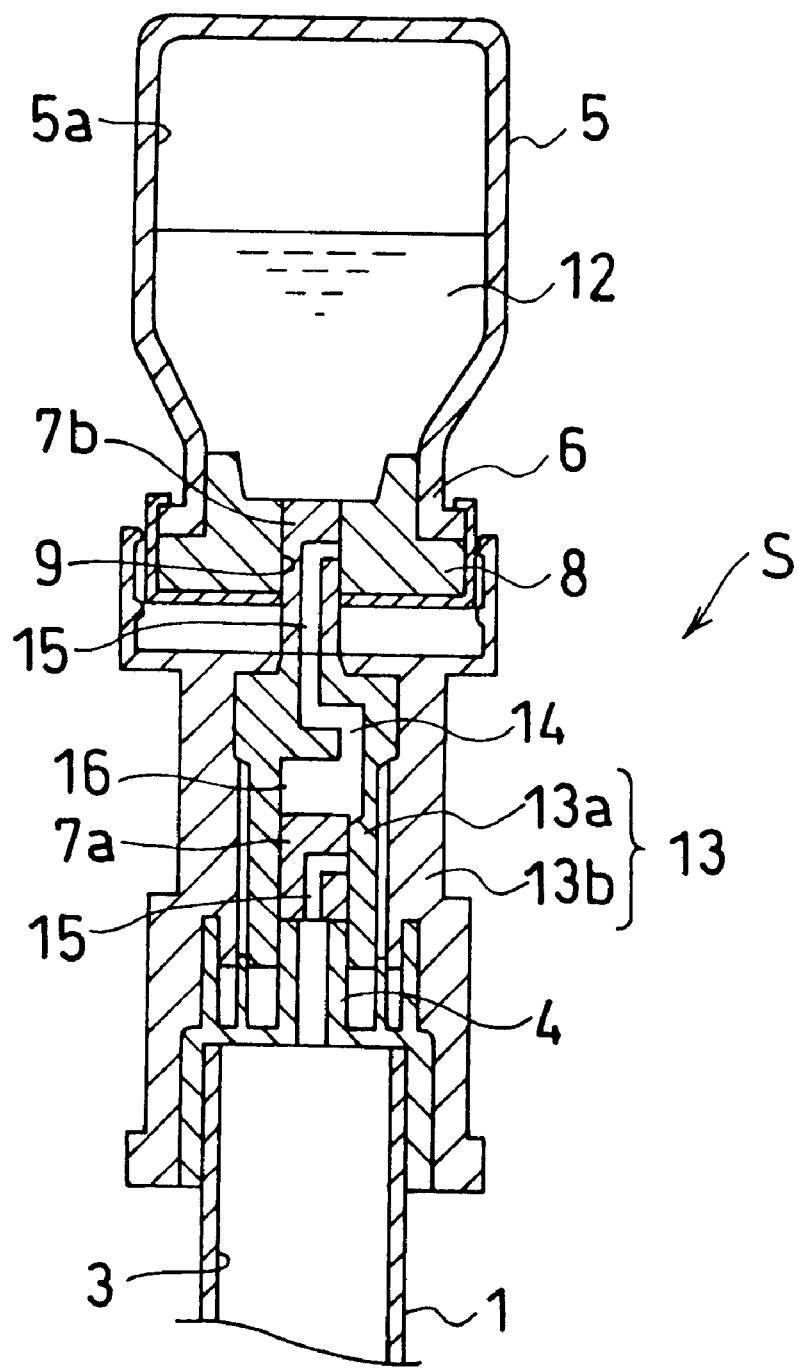
FIG. 31 illustrates a dual-chamber type injector of a fifteenth embodiment corresponding to a combination of the first invention with the third invention and is a sectional view showing its principal parts.
Figure 32:
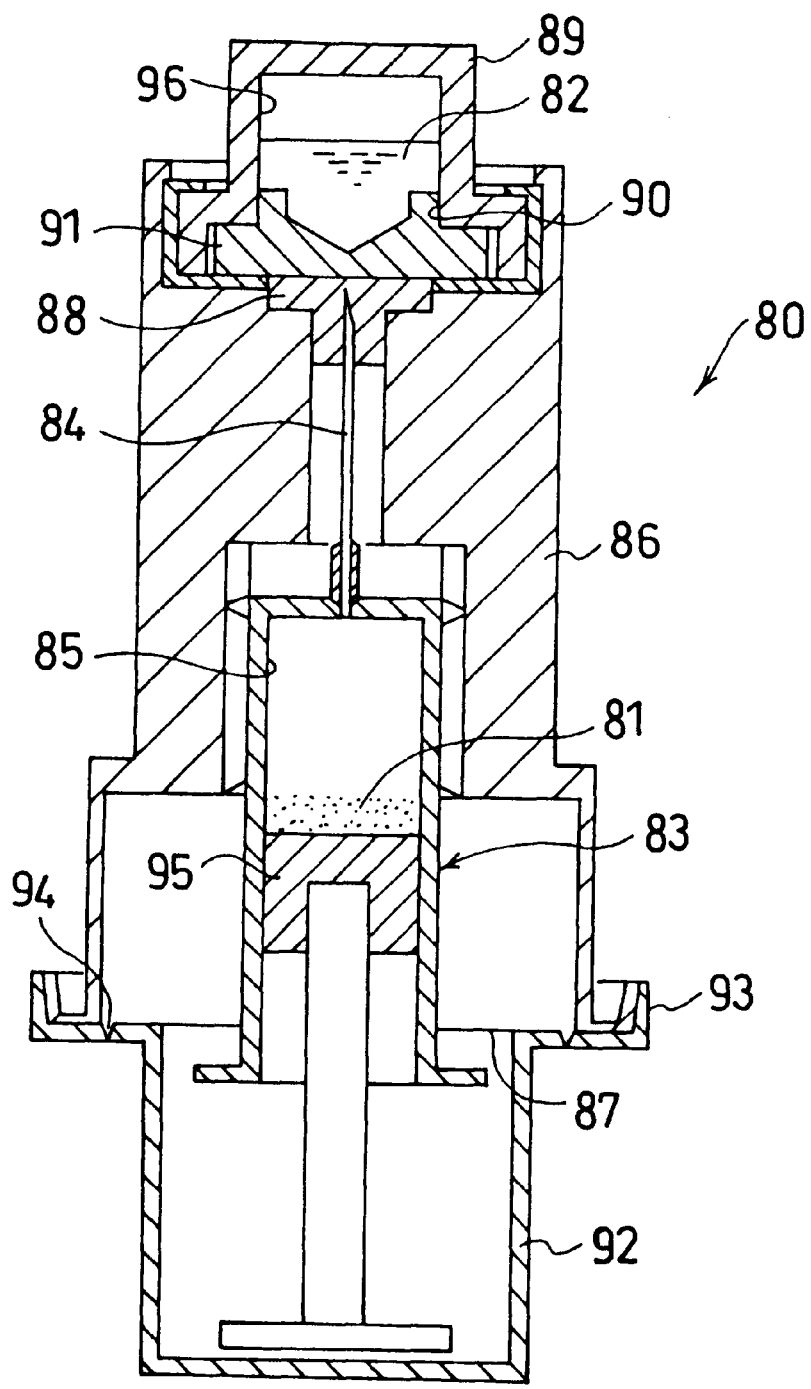
FIG. 32 illustrates prior art and corresponds to FIG. 1.

FIG. 31 illustrates a dual-chamber type injector of a fifteenth embodiment corresponding to a combination of the first invention with the third invention and is a sectional view showing its principal parts.

As shown in FIG. 31, although this fifteenth embodiment has substantially the same structure as that of the first embodiment, it differs therefrom in that a syringe 1 is attached to a connector 13 unmovably. And a first closure member 7a arranged in a communication passage 14 is adapted to move toward a container chamber 5a upon receipt of the pressure of a fluid within the syringe 1.

The mixing operation within the dual-chamber type injector (S) is effected by increasing the pressure of the fluid within the syringe 1 through pushing a piston (not shown) and meanwhile moving a hermetically closed container 5 toward the syringe 1.

In other words, the pushing of the above piston increases the pressure of the fluid within the syringe 1 to result in displacing the first closure member 7a toward the container chamber 5a and opening a communication hole 15 of the first closure member 7a within an intermediate chamber 16. On the other hand, a second closure member 7b moves within a through hole 9 like in the first embodiment to open one end of its communication hole 15 within a container chamber 5a, thereby communicating the container chamber 5a with a drug accommodating chamber 3 within the syringe 1.

What is claimed is:

1. A dual-chamber type injector apparatus comprising:
   a syringe including a drug accommodating chamber accommodating a first component and having a needle connecting portion having no injection needle attached thereto;
   a hermetically closed container including a container chamber accommodating a second component and a takeout port;
   a connector connecting and fixing said syringe and said container to each other, said needle connecting portion being arranged opposite to said takeout port, and at least said syringe being adapted to be separable from said connector;
   a communication passage capable of communicating said drug accommodating chamber of said syringe with said container chamber, said communication passage being closed by a closure member arranged between said drug accommodating chamber of said syringe and said container chamber, and at least part of said closure member being displaceable toward said container chamber in response to an increase in the inner pressure of said syringe so as to be able to open said communication passage; and
   a piston disposed within said syringe, said piston being pushable to increase the inner pressure of said syringe so as to displace at least part of said closure member toward said container chamber with the increased inner pressure so as to open said communication passage.

2. The dual-chamber type injector apparatus of claim 1, wherein said takeout port has a closure member supporting member attached thereto and said closure member is supported by said supporting member so as to be slidably movable therein.

3. The dual-chamber type injector apparatus of claim 1, wherein a rubber closure is disposed in said takeout port of said hermetically closed container, said rubber closure being provided with a through hole in which said closure member is arranged so as to be slidably movable.

4. The dual-chamber type injector apparatus of claim 3, wherein said closure member comprises an end surface having communication grooves therein and said through hole has an inner surface provided with an annular groove and vertical grooves between said container chamber and said closure member.

5. The dual-chamber type injector apparatus of claim 4, wherein said through hole comprises a closure member accommodating space located between said closure member and said container chamber, said space having a length greater than said closure member and an inner surface provided with said annular groove and said vertical grooves.

6. The dual-chamber type injector apparatus of claim 1, wherein the at least part of said closure member that is displaceable toward said container chamber in response to an increase in the inner pressure of said syringe is arranged in said communication passage so as to prevent closure thereof upon a subsequent decrease in the inner pressure of said syringe.

* * * * *